US009739698B2

United States Patent
Tanabe et al.

(10) Patent No.: US 9,739,698 B2
(45) Date of Patent: Aug. 22, 2017

(54) OPTICAL ANALYSIS DEVICE, OPTICAL ANALYSIS METHOD AND COMPUTER PROGRAM FOR OPTICAL ANALYSIS USING SINGLE LIGHT-EMITTING PARTICLE DETECTION

(71) Applicant: OLYMPUS CORPORATION, Tokyo (JP)

(72) Inventors: Tetsuya Tanabe, Tokyo (JP); Seiji Kondo, Tokyo (JP)

(73) Assignee: OLYMPUS CORPORATION, Tokyo (JP)

( * ) Notice: Subject to any disclaimer, the term of this patent is extended or adjusted under 35 U.S.C. 154(b) by 0 days.

(21) Appl. No.: 15/084,246

(22) Filed: Mar. 29, 2016

(65) Prior Publication Data

US 2016/0209315 A1    Jul. 21, 2016

Related U.S. Application Data

(63) Continuation of application No. PCT/JP2014/067339, filed on Jun. 30, 2014.

(30) Foreign Application Priority Data

Oct. 7, 2013    (JP) .................................. 2013-210550

(51) Int. Cl.
*G01N 15/06*    (2006.01)
*G02B 21/16*    (2006.01)
(Continued)

(52) U.S. Cl.
CPC ............. *G01N 15/06* (2013.01); *G01N 21/64* (2013.01); *G02B 21/008* (2013.01);
(Continued)

(58) Field of Classification Search
CPC ............... G01N 21/64; G01N 21/6408; G01N 21/6452; G01N 21/6458; G01N 21/76;
(Continued)

(56) References Cited

U.S. PATENT DOCUMENTS 4,251,733 A    2/1981    Hirleman, Jr.
5,866,336 A    2/1999    Nazarenko et al.
(Continued)

FOREIGN PATENT DOCUMENTS

EP    1 906 172 A1    4/2008
JP    4-337446 A    11/1992
(Continued)

OTHER PUBLICATIONS

International Search Report dated Sep. 22, 2014, issued in counterpart International Application No. PCT/JP2014/067339 (2 pages).
(Continued)

*Primary Examiner* — Sang Nguyen
(74) *Attorney, Agent, or Firm* — Westerman, Hattori, Daniels & Adrian, LLP

(57) ABSTRACT

In the scanning molecule counting method using optical measurement with a confocal or multiphoton microscope, there is provided a technique of computing a light-emitting particle concentration which changes with time and detecting a concentration change velocity or a reaction velocity. The inventive optical analysis technique of detecting light of light-emitting particles in a sample solution generates time series light intensity data of light from a light detection region detected with moving the position of the light detection region of the microscope in the sample solution; measures successively an interval of generation times of signals of the light-emitting particles detected in the time series light intensity data; and determines the concentration or concen-
(Continued)

tration change velocity of the light-emitting particles, using the successively measured signal generation time intervals.

12 Claims, 8 Drawing Sheets

(51) Int. Cl.
   *G02B 21/00*    (2006.01)
   *G01N 21/64*    (2006.01)
   *G01N 15/00*    (2006.01)

(52) U.S. Cl.
   CPC ..... *G02B 21/0032* (2013.01); *G02B 21/0048* (2013.01); *G02B 21/0084* (2013.01); *G02B 21/16* (2013.01); *G01N 2015/0065* (2013.01); *G01N 2015/0687* (2013.01); *G01N 2015/0693* (2013.01); *G02B 2207/114* (2013.01)

(58) Field of Classification Search
   CPC .. G01N 21/763; G02B 21/0076; G02B 21/16; G02B 21/367
   USPC .............. 356/335–343, 317–318; 250/203.3, 250/458.1, 459.1
   See application file for complete search history.

(56) References Cited

U.S. PATENT DOCUMENTS

| | | |
|---|---|---|
| 6,280,960 B1 | 8/2001 | Carr |
| 6,376,843 B1 | 4/2002 | Palo |
| 6,388,746 B1 | 5/2002 | Eriksson et al. |
| 6,388,788 B1 | 5/2002 | Harris et al. |
| 6,400,487 B1 | 6/2002 | Harris et al. |
| 6,403,338 B1 | 6/2002 | Knapp et al. |
| 6,710,871 B1 | 3/2004 | Goix |
| 6,782,297 B2 | 8/2004 | Tabor |
| 6,856,391 B2 | 2/2005 | Garab et al. |
| 6,927,401 B1 | 8/2005 | Palo |
| 8,284,484 B2 | 10/2012 | Hoult et al. |
| 8,681,332 B2* | 3/2014 | Tanabe ............... G01N 21/6458 250/458.1 |
| 9,068,944 B2* | 6/2015 | Tanabe ............... G01N 21/6408 |
| 9,188,535 B2* | 11/2015 | Hanashi ............. G01N 15/1429 |
| 2001/0035954 A1 | 11/2001 | Rahn et al. |
| 2002/0008211 A1 | 1/2002 | Kask |
| 2002/0036775 A1 | 3/2002 | Wolleschensky et al. |
| 2003/0036855 A1 | 2/2003 | Harris et al. |
| 2003/0218746 A1 | 11/2003 | Sampas |
| 2004/0022684 A1 | 2/2004 | Heinze et al. |
| 2004/0051051 A1 | 3/2004 | Kato et al. |
| 2004/0150880 A1 | 8/2004 | Nakata et al. |
| 2005/0260660 A1 | 11/2005 | van Dongen et al. |
| 2006/0078998 A1 | 4/2006 | Puskas et al. |
| 2006/0158721 A1 | 7/2006 | Nakata et al. |
| 2006/0256338 A1 | 11/2006 | Gratton et al. |
| 2008/0052009 A1 | 2/2008 | Chiu et al. |
| 2009/0159812 A1 | 6/2009 | Livingston |
| 2009/0222218 A1* | 9/2009 | Chamberlin ............... G01J 3/10 702/23 |
| 2010/0033718 A1 | 2/2010 | Tanaami |
| 2010/0177190 A1 | 7/2010 | Chiang et al. |
| 2010/0202043 A1 | 8/2010 | Ujike |
| 2012/0319009 A1 | 12/2012 | Yamaguchi |
| 2013/0228705 A1* | 9/2013 | Nishikawa ......... G01N 15/1463 250/459.1 |
| 2013/0302906 A1* | 11/2013 | Tanabe ............... G01N 21/6452 436/172 |
| 2013/0314705 A1 | 11/2013 | Tanabe et al. |
| 2014/0024020 A1 | 1/2014 | Tanabe |
| 2014/0134608 A1* | 5/2014 | Hanashi ............. G01N 21/6408 435/5 |
| 2015/0108369 A1 | 4/2015 | Hanashi |

FOREIGN PATENT DOCUMENTS

| | | |
|---|---|---|
| JP | 10-512952 A | 12/1998 |
| JP | 2002-507762 A | 3/2002 |
| JP | 2002-543414 A | 12/2002 |
| JP | 2004-506192 A | 2/2004 |
| JP | 2005-98876 A | 4/2005 |
| JP | 2005-099662 A | 4/2005 |
| JP | 2007-20565 A | 2/2007 |
| JP | 4023523 B2 | 12/2007 |
| JP | 2008-116440 A | 5/2008 |
| JP | 2008-536093 A | 9/2008 |
| JP | 2008-292371 A | 12/2008 |
| JP | 2009-145242 A | 7/2009 |
| JP | 2009-281831 A | 12/2009 |
| JP | 2009-288161 A | 12/2009 |
| JP | 2010-017127 A | 1/2010 |
| JP | 2011-002415 A | 1/2011 |
| JP | 2011-508219 A | 3/2011 |
| JP | 2013-36765 A | 2/2013 |
| WO | 98/16814 A1 | 4/1998 |
| WO | 99/47963 A1 | 9/1999 |
| WO | 00/66985 A1 | 11/2000 |
| WO | 02/12864 A1 | 2/2002 |
| WO | 2006/084283 A2 | 8/2006 |
| WO | 2007/010803 A1 | 1/2007 |
| WO | 2007/118209 A2 | 10/2007 |
| WO | 2007/147159 A2 | 12/2007 |
| WO | 2008/007580 A1 | 1/2008 |
| WO | 2008/080417 A1 | 7/2008 |
| WO | 2009/117033 A2 | 9/2009 |
| WO | 2011/108369 A1 | 9/2011 |
| WO | 2011/108370 A1 | 9/2011 |
| WO | 2011/108371 A1 | 9/2011 |
| WO | 2012/050011 A1 | 4/2012 |
| WO | 2012/099234 A1 | 7/2012 |
| WO | 2013/069504 A1 | 5/2013 |
| WO | 2013/121905 A1 | 8/2013 |

OTHER PUBLICATIONS

Park, Mira et al., "Counting the Number of Fluorophores Labeled in Biomolecules by Observing the Fluorescence-Intensity Transient of a Single Molecule" Bulletin of the Chemical Society of Japan, dated Aug. 30, 2005, vol. 78, No. 9, p. 1612-1618.
U.S. Office Action dated Apr. 2, 2013, issued in related U.S. Appl. No. 13/596,280.
Kask, Peet et al., "Two-Dimensional Fluorescence Intensity Distribution Analysis: Theory and Applications", Biophysical Journal, Apr. 2000, vol. 78, p. 1703-1713.
Chinese Office Action dated Aug. 13, 2013, issued in related Chinese application No. 201180011655.3; w/ English Translation (16 pages).
International Search Report dated Mar. 29, 2011, issued in related PCT/JP2011/053483.
International Preliminary Report on Patentability (PCT/IPEA/409) issued in related PCT/JP2011/053483.
Chinese Office Action dated Aug. 9, 2013, issued in related Chinese application No. 201180011640.7; w/ English Translation (16 pages).
International Search Report Mar. 29, 2011, issued in related PCT/JP2011/053482.
International Preliminary Report on Patentability (PCT/IPEA/409) issued in related PCT/JP2011/053482.
U.S. Office Action dated Jan. 3, 2013, issued in related U.S. Appl. No. 13/597,825.
Chinese Office Action dated Feb. 7, 2013, issued in related Chinese application No. 201180011644.5; w/ English Translation (18 pages).
Extended European Search Report dated Mar. 28, 2013, issued in related EP application No. 11750481.1.
International Search Report dated Mar. 29, 2011, issued in related PCT/JP2011/053481.
International Preliminary Report on Patentability (PCT/IPEA/409) issued in related PCT/JP2011/053481.

(56) References Cited

OTHER PUBLICATIONS

Goodwin, Peter et al., "Rapid Sizing of Individual Fluorescently Stained DNA Fragments by Flow Cytometry," Nucleic Acids Research, 1993, vol. 21, No. 4, p. 803-806.
Keller, Richard et al., "Single-Molecule Fluorescence Analysis in Solution," Applied Spectroscopy, 1996, vol. 50, No. 7, p. 12A-32A.
Lee, Yuan-Hsiang et al., "Laser-Induced Fluorescence Detection of a Single Molecule in a Capillary," Analytical Chemistry, dated Dec. 1, 1994, vol. 66, No. 23, p. 4142-4149.
Li, Haitao et al., "Ultrasensitive Coincidence Fluorescence Detection of Single DNA Molecules," Analytical Chemistry, dated Apr. 1, 2003, vol. 75, No. 7, p. 1664-1670.
Nie, Shuming et al., "Probing Individual Molecules with Confocal Fluorescence Microscopy," Science, dated Nov. 11, 1994, vol. 266, p. 1018-1021.
Tahari, Abdel. "Fluorescence Correlation Spectroscopy: Ultrasensitive Detection in Clear and Turbid Media," University of Illinois, 2006, p. 1-88.
Wu, Alan et al., "Development and Preliminary Clinical Validation of a High Sensitivity Assay for Cardiac Troponin Using a Capillary Flow (Single Molecule) Fluorescence Detector," Clinical Chemistry, 2006, vol. 52, No. 11, p. 2157-2159.
Itoh et al., "A New Method for Detection of Influenza Viruses by Single Particle-Recognition Based on the Principle of Fluorescence Correlation Spectroscopy," Chemistry and Biology, 2009, vol. 47, No. 12, p. 823-830.
Carlsson, K. et al., "Three-dimensional Microscopy Using a Confocal Laser Scanning Microscope", Optics Letters, Optical Society of America, Feb. 1985, vol. 10, No. 2, p. 53-55, XP007922413.
U.S. Office Action dated Oct. 4, 2013, issued in related U.S. Appl. No. 13/596,243.
Japanese Office Action dated Dec. 18, 2012 issued in related JP application No. 2012-503060; w/ English Translation (6 pages).
Kinjo, M. "Single Molecule Detection by Fluorescence Correlation Spectroscopy", Proteins, Nucleic Acids and Enzymes, 1999, vol. 44, No. 9, p. 1431-1438.
Guo, Xiang-Qun et al., "Use of a Long-Lifetime Re(I) Complex in Fluorescence Polarization Immunoassays of High-Molecular-Weight Analytes", Analytical Chemistry, Feb. 1998, vol. 7, No. 3, p. 632-637.

Meyer-Almes, F. J. "A New Method for Use in Molecular Diagnostics and High Throughput Pharmaceutical Screening based on Fluorescence Correlation Spectroscopy", Nanoparticle Immunoassays, R. Ridger, edit., Springer, Berlin, 2000, p. 204-224.
Kato, N. et al., "A Single Molecule Analyzer that Enables New Analysis of DNA and Protein Interactions", Gene Medicine, 2002, vol. 6, No. 2, p. 271-277.
International Search Report dated Mar. 5, 2013, issued in related PCT/JP2013/052446.
Kask, P. et al., "Fluorescence-intensity Distribution Analysis and its Application in Biomolecular Detection Technology", PNAS, vol. 96, No. 24, 1999, p. 13756-13761.
Petrasek et al. "Circular scanning fluorescence correlation spectroscopy on membranes" Optics Express, Dec. 5, 2011, vol. 19, No. 25, pp. 25006-25021, cited in Extended European Search Report dated Aug. 24, 2015 of EP Application No. 137485835.
Foldes-Papp et al. "A new concept for ultrasensitive fluorescence measurements of molecules in solution and membrane: 1. Theory and a first application" Journal of Immunological Methods, Amsterdam, NL, Mar. 2004, vol. 286, No. 1-2, (pp. 1-11), cited in Extended European Search Report dated Aug. 24, 2015 of EP Application No. 13748583.5.
Extended European Search Report dated Aug. 24, 2015, issued in EP Application No. 13748583.5. (7 pages).
Extended European Search Report dated Oct. 20, 2014, issued in related EP Application No. 12770835.2 (10 pages).
Translation of Written Opinion dated Sep. 22, 2014, issued in counterpart International Application No. PCT/JP2014/067339. (5 pages).
English translation of Written Opinion by ISA of International Application No. PCT/JP2013/052446 (Form PCT/ISA/237) mailed Mar. 5, 2013 with ISR (Form PCT/ISA/210) (6 pages).
Final Office Action dated Sep. 28, 2015 issued in co-pending U.S. Appl. No. 13/746,968.
Final Office Action dated Sep. 29, 2015 issued in co-pending U.S. Appl. No. 13/946,091.
Non-Final Office Action dated Apr. 15, 2016 issued in co-pending U.S. Appl. No. 14/451,021.

\* cited by examiner

FIG.1A
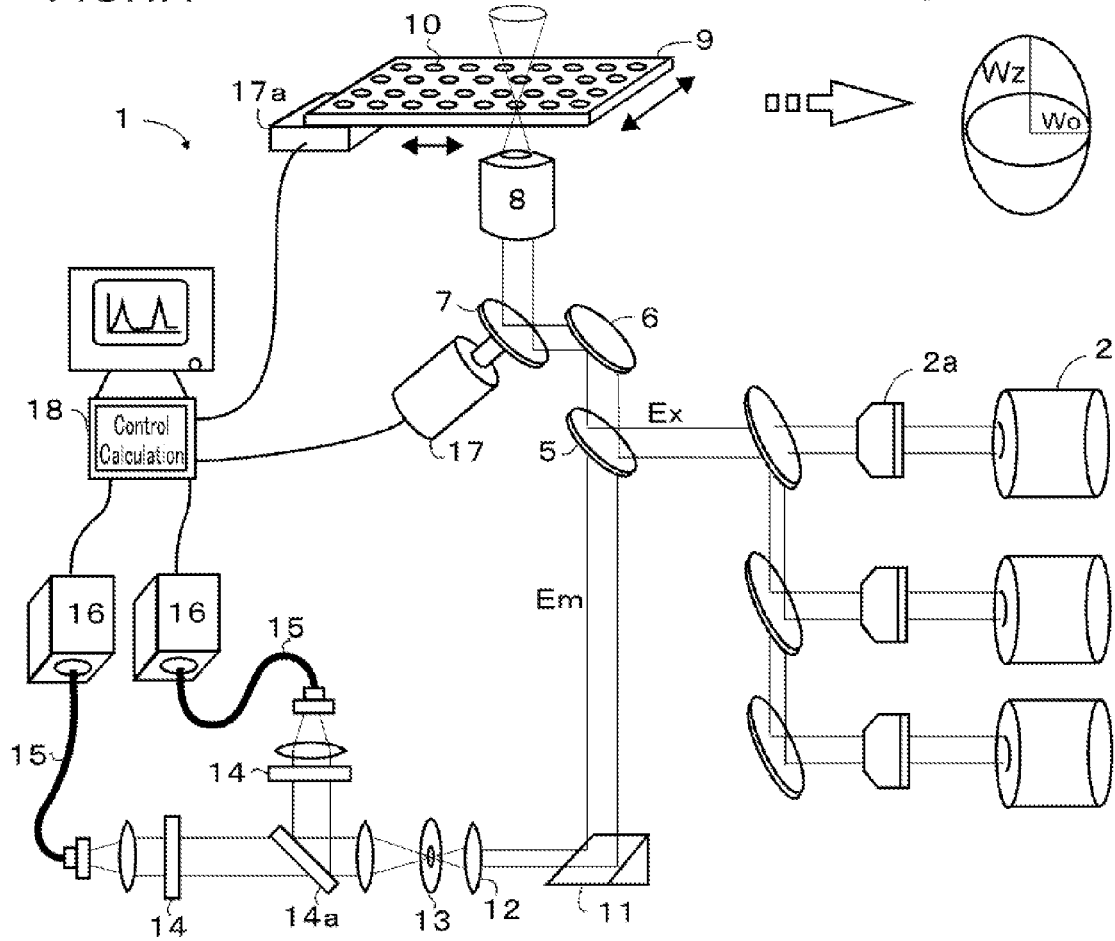
FIG.1B
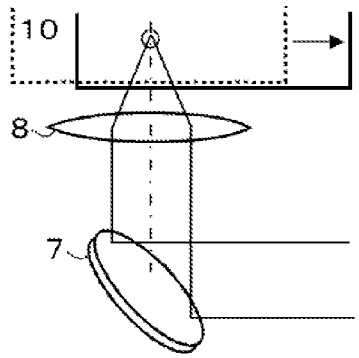
FIG.1C
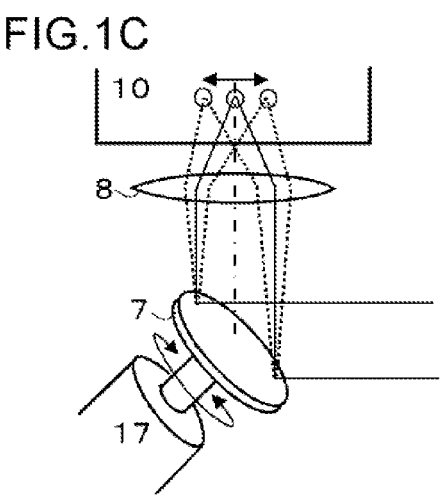
FIG.1D

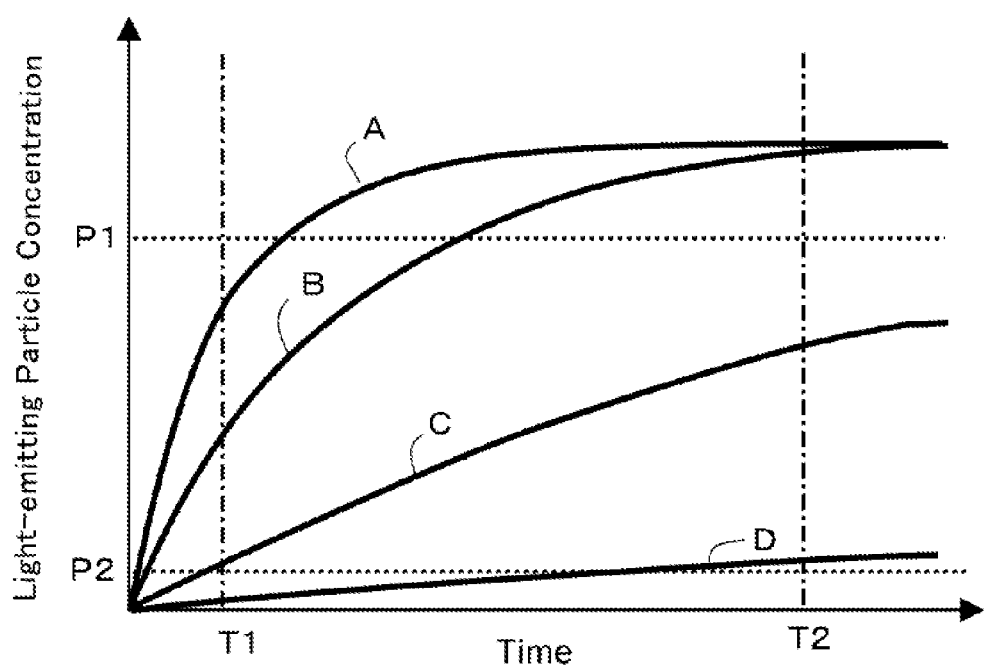

US 9,739,698 B2

OPTICAL ANALYSIS DEVICE, OPTICAL ANALYSIS METHOD AND COMPUTER PROGRAM FOR OPTICAL ANALYSIS USING SINGLE LIGHT-EMITTING PARTICLE DETECTION

TECHNICAL FIELD

This invention relates to an optical analysis technique capable of detecting light from a particulate object, e.g. an atom, a molecule or an aggregate thereof (Hereafter, these are called a "particle".), such as a biological molecule, for example, protein, peptide, nucleic acid, lipid, sugar chain, amino acid or these aggregate, virus and cell, etc., or a non-biological particle, dispersed or dissolved in a solution, by using an optical system, such as the optical system of a confocal microscope or a multiphoton microscope, which can detect light from a micro region in a solution, to acquire useful information in an analysis of conditions (an interaction, a binding or dissociating condition, etc.) of particles, and more specifically, relates to an optical analysis device, an optical analysis method and a computer program for optical analysis, which detect individually the light from a single particle which emits light, using an optical system as described above, to make it possible to conduct various optical analyses. In this regard, in this specification, a particle which emits light (hereafter, referred to as a "light-emitting particle") may be any of a particle which emits light by itself and a particle to which an arbitrary light-emitting label or light-emitting probe has been attached, and the light emitted from a light-emitting particle may be fluorescence, phosphorescence, chemiluminescence, bioluminescence, scattered light, etc.

BACKGROUND ART

According to the developments in optical measurement techniques in recent years, detection and/or measurement of faint light at a single photon or single fluorescent molecule level have become possible by using an optical system of a confocal microscope and a super high sensitive light detection technique capable of the photon counting (single photon detection). Thus, there are variously proposed optical analysis techniques of performing detection of a characteristic, an intermolecular interaction, a binding or dissociating reaction of a biological molecule, etc. by means of such a faint light measurement technique. As such optical analysis techniques, for examples, there are known Fluorescence Correlation Spectroscopy (FCS, see e.g. patent documents 1-3 and non-patent documents 1-3), Fluorescence Intensity Distribution Analysis (FIDA, e.g. patent document 4, non-patent document 4) and Photon Counting Histogram (PCH, e.g. patent document 5). In addition, in patent documents 6-8, there are proposed methods of detecting fluorescent substances based on a time progress of fluorescence signals of a sample solution measured using the optical system of a confocal microscope.

Furthermore, in patent documents 9-12, Applicant of the present application has proposed a novel optical analysis technique, using an optical system which is capable of detecting the light from a micro region in a solution, such as an optical system of a confocal microscope or a multiphoton microscope, and employing a different principle from optical analysis techniques, such as FCS and FIDA. In the case of the novel optical analysis technique (Hereinafter, referred to as "Scanning Molecule Counting Method".), the position of a micro area which is a detected region of light in a sample solution (Hereinafter, referred to as a "light detection region". When excitation light is used, it almost coincides the condensing region of the excitation light.) is moved, i.e., the inside of the sample solution is scanned with the light detection region, and when the light detection region encompasses a light-emitting particle being dispersed and moving at random in the sample solution, the light emitted from the light-emitting particle is individually detected, and thereby each of the light-emitting particles in the sample solution is detected individually so that it becomes possible to perform the counting of the light-emitting particles and the acquisition of the information about the concentration or number density of the light-emitting particles in the sample solution.

PRIOR TECHNICAL DOCUMENTS

Patent Documents

Patent document 1: Japanese Patent laid-open publication No. 2005-098876
Patent document 2: Japanese Patent laid-open publication No. 2008-292371
Patent document 3: Japanese Patent laid-open publication No. 2009-281831
Patent document 4: Japanese Patent No. 4023523
Patent document 5: WO 2008-080417
Patent document 6: Japanese Patent laid-open publication No. 2007-20565
Patent document 7: Japanese Patent laid-open publication No. 2008-116440
Patent document 8: Japanese Patent laid-open publication No. 4-337446
Patent document 9: WO2011/108369
Patent document 10: WO2011/108370
Patent document 11: WO2011/108371
Patent document 12: WO2012/099234

SUMMARY OF INVENTION

Technical Problem

By the way, in the detection or analysis of a concentration or other conditions of a particle in a solution (an interaction, a binding or dissociating condition, etc.), a changing velocity of the particle concentration or a reaction velocity of a reaction related to the particle becomes useful information. However, in the scanning molecule counting method so far, when the concentration of a light-emitting particle used as an object to be observed in a sample solution changes with time, it could be difficult to detect the light-emitting particle concentration or its changing velocity with sufficient accuracy.

As described in the above-mentioned documents, in the scanning molecule counting method so far, typically, in one manner, an optical measurement is performed for an arbitrarily set measurement time while moving a light detection region in a sample solution, and then, signals of light-emitting particles detected in the data of the light intensity values acquired in time series (time series light intensity data) are counted (Patent documents 9-11); or in an alternative manner, an optical measurement while moving a light detection region in a sample solution is performed together with detecting and counting signals of light-emitting particles in the time series light intensity data until an arbitrarily set number of particles have been detected (Patent document 12). Then, the concentration of the light-emitting particle is computed from the detected number in the set measurement time in the case of the former case, and computed from the measurement time taken for the detection of the set number of the particles in the latter case.

However, in a case that the concentration of a light-emitting particle which is an object to be observed is unknown or changes with time, in the manner of performing an optical measurement for a fixed measurement time or till a fixed number of particles have been detected, the concentration value or its changing velocity computed from a detected result may not be acquired with sufficient accuracy, depending on the set measurement time or the set number of signals to be detected.

For example, as shown in FIG. 9, in the manner of performing an optical measurement for a fixed measurement time, when the set measurement time is comparatively short (T1), the concentration may become high enough to be detectable for a light-emitting particle of which the concentration increases quickly (A, B, C), while, with respect to a light-emitting particle of which the concentration increases slowly (D), the concentration could be too low to detect without difficulty. Then, if the measurement time is set comparatively long (T2), although the concentration increases to a detectable level in the light-emitting particle of which the concentration increases slowly (D), the optical measurement for the light-emitting particle of which the concentration increases quickly will be performed for longer time than needed. Further, in a case of a light-emitting particle of which the concentration increases especially quickly (A, B), since the concentration has increased to its saturation, the time variation of the light-emitting particle concentration cannot be caught. On the other hand, in the manner of performing an optical measurement until a fixed number of particles have been detected, if the set number of particles to be detected is comparatively large (P1), the measurement for a light-emitting particle of which the concentration increases quickly (A, B, C) can be completed within a comparatively short time, while the measurement time taken for the detection can become very long for a light-emitting particle of which the concentration increases slowly (D). Then, if the set number of particles to be detected is made small (P2), the measurement time taken for the detection becomes long enough to be obtained as a significant value for a light-emitting particle of which the concentration increases slowly (D), the measurement time taken for the detection for a light-emitting particle of which the concentration increases quickly (A, B, C) becomes too short, so that it can become difficult to obtain its value with sufficient accuracy. Furthermore, the difference in the measurement time taken for the detection between a light-emitting particle of which the concentration increases quickly (A, B, C) and a light-emitting particle of which the concentration increases slowly (D) becomes a sufficiently large, significantly detectable value, because of their difference in concentration change velocity, but it is difficult to detect the difference in concentration change velocity among light-emitting particles of which the concentration increase quickly (A, B, C) with sufficient accuracy, because the measurement time lengths taken for the detection become too short.

Namely, in the scanning molecule counting method, in a case of performing an optical measurement for a fixed measurement time or until a fixed number of particles have been detected as noted above, it is desirable to set an appropriate measurement time length or an appropriate number of signals to be detected through predicting the concentration of a light-emitting particle to be observed; however, it is difficult to set the measurement time or the number of signals to be detected appropriate for the detection of the particle concentration in a system where a light-emitting particle concentration changes, and in that case, it becomes difficult to detect a concentration change velocity or a reaction velocity, also. Moreover, in a case that a light-emitting particle of which the concentration change velocity or reaction velocity varies during preforming an optical measurement, it becomes much more difficult to detect the concentration of the light-emitting particle or its change with sufficient accuracy in the manner of performing an optical measurement for a fixed measurement time or until a fixed number of particles have been detected.

Thus, a main object of the present invention is to provide a new optical analysis technique by the scanning molecule counting method, making it possible to compute a concentration or detect a concentration change velocity or a reaction velocity for a light-emitting particle even in a case that the concentration of the light-emitting particle to be observed changes with time.

Solution to Problems

According to one manner of the present invention, the above-mentioned object is achieved by an optical analysis device which detects light from light-emitting particles dispersed and moving at random in a sample solution using an optical system of a confocal microscope or a multiphoton microscope, comprising: a light detection region mover which moves a position of a light detection region of the optical system of the microscope in the sample solution; a light detector which detects light from the light detection region; and a signal processor which generates time series light intensity data of the light from the light detection region detected with the light detector during the moving of the position of the light detection region in the sample solution and detects each of signals of the light-emitting particles individually in the time series light intensity data; wherein the signal processor measures successively an interval of generation times of the signals of the light-emitting particles detected in the time series light intensity data along time progress of the time series light intensity data, and determines an index value representing a concentration of the light-emitting particles using a plurality of the signal generation time intervals measured successively.

In this structure, "light-emitting particles dispersed and moving at random in a sample solution" may be particles, such as atoms, molecules or aggregates of these, which are dispersed or dissolved in a sample solution and emit light, and those may be arbitrary particulate matters making the Brownian motion freely in the solution without being fixed on a substrate, etc. The light-emitting particles are typically fluorescent particles, but may be particles which emit light by phosphorescence, chemiluminescence, bioluminescence, light scattering, etc. Moreover, especially in the present invention, the light-emitting particles to be observed may be particles of which the concentration changes with time progress. The "light detection region" of the optical system of the confocal microscope or multiphoton microscope is the micro region where light is detected in those microscopes, which region corresponds to the region to which illumination light is condensed when the illumination light is given from an objective (Especially in a confocal microscope, this region is determined in accordance with the spatial relationship of an objective and a pinhole. For light-emitting particles which emit light without illumination light, for example, molecule which emit light according to chemiluminescence or bioluminescence, no illumination light is required in the microscope.). Further, typically, the light detector detects the light from the light detection region by the photon counting in which (a) photon(s) arriving in every predetermined measuring unit time (bin time) is/are counted, and in that case, the time series light intensity data becomes time series photon count data. In this connection, in this specification, "a signal of a light-emitting particle" means a signal expressing light from a light-emitting particle, unless noted otherwise.

As understood from the above, in the basic structure of the above-mentioned present invention, i.e., the scanning molecule counting method, the light detection is sequentially performed while the position of the light detection region is moved in a sample solution, namely, while the inside of the sample solution is scanned with the light detection region. Then, when the light detection region moving in the sample solution encompasses a randomly moving light-emitting particle, the light from the light-emitting particle is detected by the light detector and thereby the existence of one particle will be detected. Thus, in the sequentially detected, time series light intensity data, a signal from a light-emitting particle is individually detected, and thereby, the existences of individual particles are detected one by one successively, and accordingly, diverse information on the conditions of the particles in the solution will be acquired. In this structure, regarding the signals of the light-emitting particles detected successively in time series light intensity data, as explained in detail later, as the concentration of the light-emitting particles in the sample solution is higher, the interval of the generation times of the signals of the light-emitting particles, generated one by one, becomes shorter. Namely, when the concentration of the light-emitting particles in the sample solution changes during performing the optical measurement, the interval of the generation times of the signals of the light-emitting particles will change, corresponding to the concentration change. Then, in the above-mentioned present invention, further, in the signal processor, the interval of the generation times of the signals of the light-emitting particles detected in time series light intensity data along time progress of the time series light intensity data is successively measured, and the index value representing the concentration of the light-emitting particles is determined, using a plurality of the signal generation time intervals measured successively. Here, the "index value representing the concentration of the light-emitting particles" may be the concentration value itself or an arbitrary value convertible into the concentration. According to this structure, even in a case that the concentration of a light-emitting particles to be observed changes with time, it becomes possible to track the light-emitting particle concentration or its index value successively in time series.

Further, according to the above-mentioned structure, it becomes possible to track the time variation of the concentration of the light-emitting particles or its index value. Thus, in the above-mentioned inventive device, the signal processor may be designed to determine an index value representing a changing velocity of the concentration of the light-emitting particles using a plurality of the signal generation time intervals measured successively. In this regard, the "index value representing a changing velocity of the concentration" may be the changing velocity value itself or an arbitrary value convertible into the changing velocity value. According to this structure, values of the changing velocity of a particle concentration and/or a reaction velocity of a reaction relating to the particles in various phenomena relating to particles, such as a structural change, an interaction, a binding and dissociation reaction, becomes acquirable, and these become useful information in the detection or analysis of a phenomenon relating to the particles.

Further, the concentration values of the light-emitting particles or the index values or the concentration changing velocity values or its index values, obtained momentarily with the plurality of the successively measured signal generation time intervals can be used for estimating or determining a concentration value or its index value of the light-emitting particles to be observed at an arbitrary time, such as an initial concentration or a saturated concentration in a concentration change, a reaction, etc. Thus, in the above-mentioned inventive device, the signal processor may be designed to determine an index value representing a concentration of the light-emitting particles at an arbitrary time using the plurality of the successively measured signal generation time intervals.

In this regard, in the above-mentioned structure, the interval of the generation times of the signals of the light-emitting particles measured successively may be an interval in which an arbitrarily set number of the signals of the light-emitting particles have been generated. For example, the signal generation time interval of the light-emitting particles may be a time interval from the generation of one signal to the generation of the just next signal, or a time interval until a plurality of signals have been generated from the generation of one signal. The arbitrarily set number may be changed in one time of the optical measurement as long as the number is grasped.

The optical analysis technique of conducting a light detection with moving the position of a light detection region in a sample solution and detecting the signal from each light-emitting particle individually in the above-mentioned inventive device, comprising the processes of successively measuring an interval of generation times of signals of the light-emitting particles and the process of determining a concentration or a concentration change velocity of the light-emitting particles with the successively measured signal generation time intervals can be realized with a general-purpose computer. Thus, according to another aspect of the present invention, there is provided a computer readable storage device having a computer program product including programmed instructions for optical analysis of detecting light from light-emitting particles dispersed and moving at random in a sample solution using an optical system of a confocal microscope or a multiphoton microscope, said programmed instructions causing a computer to perform steps of: moving a position of a light detection region of the optical system of the microscope in the sample solution; measuring a light intensity from the light detection region during the moving of the position of the light detection region in the sample solution to generate time series light intensity data; detecting individually signals of the light-emitting particles in the time series light intensity data; measuring successively an interval of generation times of the signals of the light-emitting particles detected in the time series light intensity data along time progress of the time series light intensity data; and determining an index value representing a concentration of the light-emitting particles using a plurality of the signal generation time intervals measured successively. In this regard, the computer program is provided while being memorized in a computer readable storage medium. A computer reads out the program memorized in the storage device and realizes the above-mentioned steps by performing the processing and calculations of information. Here, a computer readable storage device may be a magnetic disc, a magnetic optical disk, a CD-ROM, a DVD-ROM, a semiconductor memory, etc. Furthermore, the above-mentioned program may be distributed to a computer through communication line, and the computer which received this distribution may be made to execute the program.

Also in this structure, there may be provided a step of computing an index value representing a changing velocity of the concentration of the light-emitting particles using a plurality of the successively measured signal generation time intervals, and in the step of determining an index value representing the concentration of the light-emitting particles, an index value representing a concentration of the light-emitting particles at an arbitrary time in the time series light intensity data may be determined using the successively measured signal generation time intervals. Further, the intervals of the generation times of the signals of the light-emitting particles may be a time interval in which a predetermined number of the signals of the light-emitting particles have been generated.

Furthermore, according to the above-mentioned inventive device or computer program, there is realized an optical analysis method of conducting light detection with moving the position of a light detection region in a sample solution and detecting signals of light-emitting particles individually, in which intervals of generation times of the signals of the light-emitting particles are measured successively, and a concentration or a concentration change velocity of the light-emitting particles is determined using the successively measured signal generation time intervals. Thus, according to the present invention, there is further provided an optical analysis method of detecting light from light-emitting particles dispersed and moving at random in a sample solution using an optical system of a confocal microscope or a multiphoton microscope, comprising steps of: moving a position of a light detection region of the optical system of the microscope in the sample solution; measuring a light intensity from the light detection region during the moving of the position of the light detection region in the sample solution to generate time series light intensity data; detecting individually signals of the light-emitting particles in the time series light intensity data; measuring successively an interval of generation times of the signals of the light-emitting particles detected in time series light intensity data along time progress of the time series light intensity data; and determining an index value representing a concentration of the light-emitting particles using a plurality of the signal generation time intervals measured successively.

Also in this structure, there may be provided a step of computing an index value representing a changing velocity of the concentration of the light-emitting particles using a plurality of the successively measured signal generation time intervals, and in the step of determining an index value representing the concentration of the light-emitting particles, an index value representing a concentration of the light-emitting particles at an arbitrary time in the time series light intensity data may be determined using the successively measured signal generation time intervals. Further, the intervals of the generation times of the signals of the light-emitting particles may be a time interval in which a predetermined number of the signals of the light-emitting particles have been generated.

The optical analysis technique of the above-mentioned present invention is used, typically, for an analysis of a condition in a solution of a biological particulate object, such as a biological molecule, e.g. a protein, a peptide, a nucleic acid, a lipid, a sugar chain, an amino acid or these aggregate, a virus and a cell, etc., but it may be used for an analysis of a condition in a solution of a non-biological particle (for example, an atom, a molecule, a micelle, a metallic colloid, etc.), and it should be understood that such a case belongs to the scope of the present invention also. The way and manner of moving the position of a light detection region relative to a sample solution, the way and manner of extracting or detecting the signal of each light-emitting particle from the light intensity value in time series light intensity data, the way and manner of determining parameters for determining an absolute concentration value, etc. may be similar to ways and manners described in patent documents 9-12, etc.

Effect of Invention

According to the scanning molecule counting method in which an optical measurement is performed for a fixed measurement time or until a fixed number of particles have been detected as described in patent documents 9-12, etc., the counting of the light-emitting particles and/or the determination of their concentration can be performed with sufficient accuracy in a case that the light-emitting particle concentration in a sample solution is in a quasi-static state or in a steady state. On the other hand, as in the present invention, according to a manner of successively determining or estimating the concentration values, the concentration change velocities or those index values of the light-emitting particles with reference to the signal generation time intervals of the light-emitting particles detected successively, in a case of a system in which the light-emitting particle concentration in a sample solution changes with time, i.e., in a case that the light-emitting particle concentration is in a dynamic state, it becomes possible to track the change of the light-emitting particle concentration or the change of the concentration change velocity in time series. Further, in the case of the present invention, since it becomes possible to track the behavior of the concentration change of a light-emitting particle, it becomes possible to estimate a concentration value or its index value of the light-emitting particle at a time when no optical measurement is actually conducted. Furthermore, in the present invention, there is no need to set beforehand the measurement time or the number of particles to be detected for an optical measurement, and even if the concentration of a light-emitting particle to be observed is not grasped at a certain degree beforehand, the determination or estimation of the concentration value or its index value of the light-emitting particle can be achieved so that the necessity of performing exploratory experiments or trials and errors for the setting of the measurement time or the number of particles to be detected for an optical measurement will be reduced, and therefore, it is advantageous in that the amounts of a sample solution and light-emitting particles to be used can be saved. Namely, the structure of the present invention may be applied to when a light-emitting particle concentration in a sample solution is in a quasi-static or steady state, and also in that case, the amounts of the sample solution and light-emitting particles to be used for exploratory experiments or trial and error can be saved. Furthermore, in the present invention, since it becomes possible to detect a concentration change velocity of a light-emitting particle or a reaction velocity of a reaction related to a light-emitting particle, useful information in analyzing a condition of particles, which has not been acquired easily by the scanning molecule counting method so far, will be acquired.

Other purposes and advantages of the present inventions will become clear by explanations of the following preferable embodiments of the present invention.

BRIEF DESCRIPTIONS OF DRAWINGS

FIG. 1A is a schematic diagram of the internal structure of an optical analysis device with which the scanning molecule counting method is performed according to the present invention. FIG. 1B is a schematic diagram of a confocal volume (an observation region of a confocal microscope). FIG. 1C is a schematic diagram of the mechanism for changing the direction of a mirror 7 to move the position of a light detection region in a sample solution. FIG. 1D is a schematic diagram of the mechanism which moves the horizontal position of a micro plate to move the position of a light detection region in a sample solution.

FIGS. 2A and 2B are a schematic diagram explaining the principle of the light detection and a schematic diagram of the variation of the measured light intensity with time in the scanning molecule counting method to which the present invention is applied, respectively. FIG. 2C is a drawing explaining about the principle of determining a light-emitting particle concentration through measuring signal generation time intervals of light-emitting particles. FIG. 2D is a schematic drawing of the region through which a light detection region passes.

FIG. 3A is a drawing showing procedures of the scanning molecule counting method performed according to the present invention in the form of flow chart, and FIG. 3B is a drawing showing procedures from an optical measurement to a detection of a light-emitting particle signal in the form of flow chart.

FIGS. 4A and 4B are drawings of models in a case that a light-emitting particle crosses a light detection region owing to the Brownian motion and in a case that a light-emitting particle crosses a light detection region by moving the position of the light detection region in a sample solution at a velocity quicker than the diffusional moving velocity of the light-emitting particle. FIG. 4C shows drawings explaining an example of the signal processing step of the detected signals in the procedure for detecting the existence of a light-emitting particle from the measured time series light intensity data (change in time of photon count) in accordance with the scanning molecule counting method.

Figure 8A:
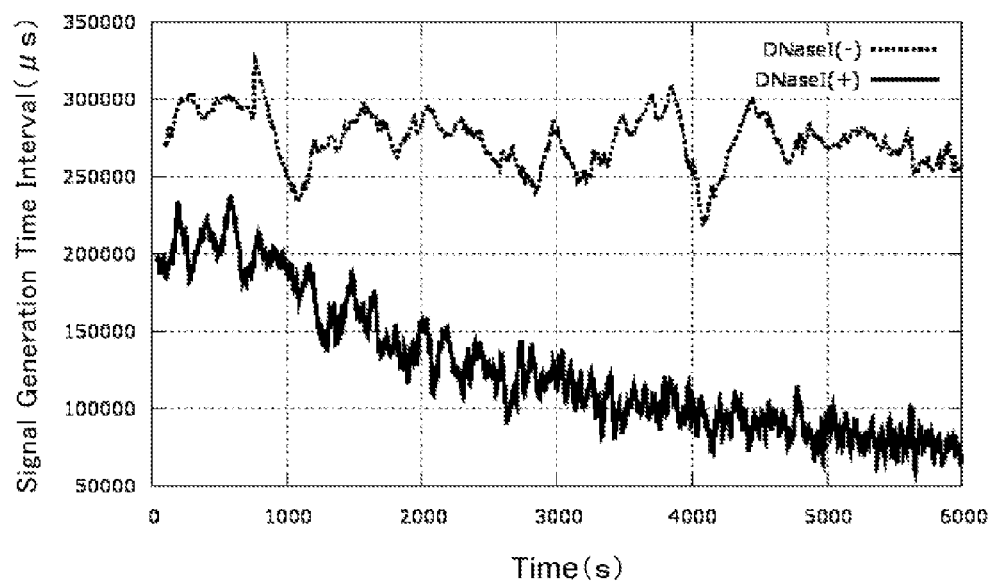
Figure 8B:
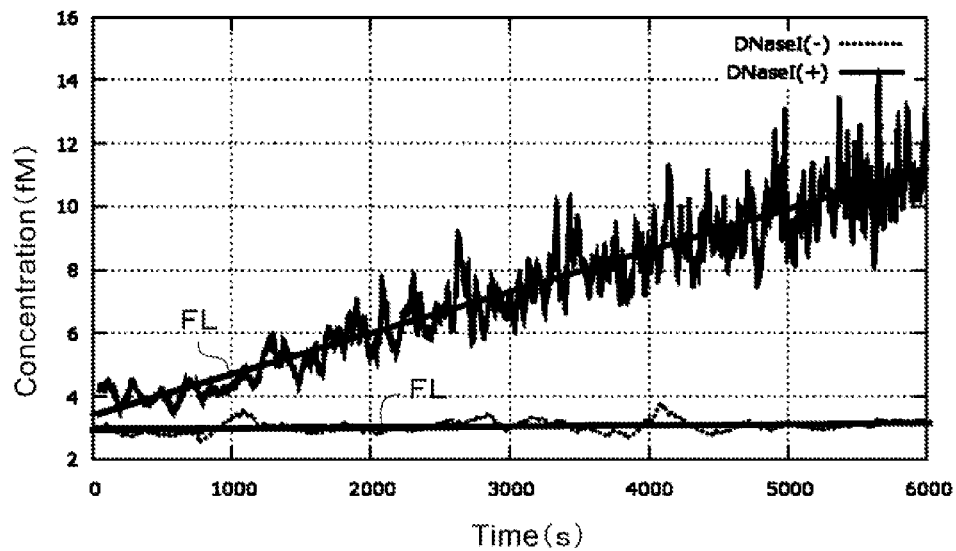

FIG. 8A shows a time variation of the generation time intervals of light-emitting particle signals (the time interval of generations of 50 particles) obtained in Embodiment 1, and FIG. 8B shows a time variation of a light-emitting particle concentration converted from the generation time intervals of the light-emitting particle signals. Here, the ordinate axis of the generation time interval in FIG. 8A indicates the value of 1/50 of the measured generation time interval of 50 particles.

FIG. 9 is a drawing showing schematically a time variation of a concentration of a light-emitting particle of which the concentration changes with time, explaining about conditions in results detected in manners of performing an optical measurement for a fixed measurement time (T1, T2) and until a fixed number (P1, P2) of particles have been detected in the scanning molecule counting method.

EXPLANATIONS OF REFERENCE NUMERALS

1 - - - Optical analysis device (confocal microscope)
2 - - - Light source
3 - - - Single mode optical fiber
4 - - - Collimating lens
5 - - - Dichroic mirror
6, 7, 11 - - - Reflective mirror
8 - - - Objective
9 - - - Micro plate
10 - - - Well (sample solution container)
12 - - - Condenser lens
13 - - - Pinhole
14 - - - Barrier filter
14a - - - Dichroic mirror or Polarization beam splitter
15 - - - Multi-mode optical fiber
16 - - - Photodetector
17 - - - Mirror deflector
17a - - - Stage position changing apparatus
18 - - - Computer

DESCRIPTION OF EMBODIMENTS

In the followings, preferable embodiments of the present invention are described in detail.

Structure of Optical Analysis Device

In the basic structure, an optical analysis device which realizes the optical analysis technique according to the present invention is a device constructed by associating the optical system of a confocal microscope and a photodetector, enabling the scanning molecule counting method as described in patent documents 9-12 or FCS, FIDA, etc., as schematically illustrated in FIG. 1A. Referring to this drawing, the optical analysis device 1 consists of an optical system 2-17 and a computer 18 for acquiring and analyzing data together with controlling the operation of each part in the optical system. The optical system of the optical analysis device 1 may be the same as the optical system of a usual confocal microscope, where laser light, emitted from a light source 2 and transmitted through the inside of a single mode fiber 3 (Ex), forms light diverging to be radiated at the angle decided by an inherent NA at the emitting end of the fiber; and after forming a parallel beam with a collimator 4, the light is reflected on a dichroic mirror 5 and reflective mirrors 6 and 7, entering into an objective 8. Above the objective 8, typically, there is placed a sample container or a micro plate 9 having wells 10 arranged thereon, to which one to several tens of μL of a sample solution is dispensed, and the laser light emitted from the objective 8 is focused in the sample solution in the sample container or well 10, forming a region having strong light intensity (excitation region). In the sample solution, light-emitting particles to be observed objects, which are typically fluorescent particles or particles to which a light emitting label such as a fluorescent dye is attached, are dispersed or dissolved, and when such a light-emitting particle enters into the excitation region, the light-emitting particle is excited and emits light during dwelling in the excitation region. The emitted light (Em), after passing through the objective 8 and the dichroic mirror 5, is reflected on the mirror 11 and condensed by a condenser lens 12, and then the light passes through the pinhole 13; transmits through the barrier filter 14 (where a light component only in a specific wavelength band is selected); and is introduced into a multimode fiber 15, reaching to the corresponding photodetector 16, and after the conversion into time series electric signals, the signals are inputted into the computer 18, where the processes for optical analyses are executed in manners explained later. In this regard, as known in ones skilled in the art, in the above-mentioned structure, the pinhole 13 is located at a conjugate position of the focal position of the objective 8, and thereby only the light emitted from the focal region of the laser light, i.e., the excitation region, as schematically shown in FIG. 1B, passes through the pinhole 13 while the light from regions other than the excitation region is blocked. The focal region of the laser light illustrated in FIG. 1B is a light detection region, whose effective volume is usually about 1-10 fL in this optical analysis device (typically, the light intensity is spread in accordance with a Gaussian type distribution having the peak at the center of the region. The effective volume is a volume of an approximate ellipsoid bordering a surface where the light intensity is reduced to $1/e^2$ of the center light intensity.), which focal region is called as "confocal volume". Furthermore, in the present invention, since the light from a single light-emitting particle, for example, the faint light from one fluorescent dye molecule is detected, preferably, a super high sensitive photodetector, usable for the photon counting, is used for the photodetector 16. When the detection of light is performed by the photon counting, the measurement of light intensity is performed for a predetermined time in a manner of measuring the number of photons which have sequentially arrived at a photodetector in every measuring unit time (BIN TIME). Thus, in this case, the time series light intensity data is time series photon count data. Also, on the stage (not shown) of the microscope, there may be provided a stage position changing apparatus 17a for moving the horizontal position of the micro plate 9, in order to change the well 10 to be observed. The operation of the stage position changing apparatus 17a may be controlled by the computer 18. According to this structure, quick measurements can be achieved even when there are two or more specimens.

Furthermore, in the optical system of the above-mentioned optical analysis device, there is further provided a mechanism for changing the optical path of the optical system to scan the inside of the sample solution with the light detection region, namely to move the position of the focal region i.e., the light detection region, within the sample solution. For this mechanism for moving the position of the light detection region, for example, there may be employed a mirror deflector 17 which changes the direction of the reflective mirror 7, as schematically illustrated in FIG. 1C (the type of moving the absolute position of a light detection region). This mirror deflector 17 may be the same as that of a galvanomirror device equipped on a usual laser scan type microscope. Or, alternatively, as illustrated in FIG. 1D, the stage position changing apparatus 17a may be operated in order to move the horizontal position of the container 10 (micro plate 9), into which the sample solution has been dispensed, to move the relative position of the light detection region in the sample solution (the type of moving the absolute position of a sample solution). Moreover, together with making the light detection region circulate along a scanning track in the way of moving the absolute position of a light detection region by changing the optical path, the position of the scanning track of the light detection region in the sample solution may be moved along a predetermined moving route in the way of moving the position of the sample solution. In either of the ways, in order to attain a desired moving pattern of the position of the light detection region, the mirror deflector 17 and/or the stage position changing apparatus 17a is driven in harmony with the light detection of the photodetector 16 under the control of the computer 18. The scanning track of the position of the light detection region may be a closed cyclic route, such as a circle, an ellipse, etc., and the moving route of the position of the sample solution may be arbitrarily selected from circular, elliptical, straight and curvilinear ones and a combination of these (The program in the computer 18 may be designed so that various moving patterns can be selected.) In this regard, although not illustrated, the position of the light detection region may be moved in the vertical direction by moving the objective 8 or stage up and down.

In a case that a light-emitting particle to be an object to be observed emits light by multiple photon absorption, the above-mentioned optical system is used as a multiphoton microscope. In that case, since the light is emitted only from the focal region of the excitation light (light detection region), the pinhole 13 may be removed. Further, in a case that a light-emitting particle to be an object to be observed emits light owing to a chemiluminescence or bioluminescence phenomenon without excitation light, the optical system 2-5 for generating excitation light may be omitted. When a light-emitting particle emits light owing to phosphorescence or scattered light, the above-mentioned optical system of the confocal microscope is used as it is. Furthermore, in the optical analysis device 1, as shown in the drawing, two or more excitation light sources 2 may be provided so that the wavelength of the excitation light can be appropriately selected in accordance with the wavelength of the light for exciting a light-emitting particle. Similarly, two or more photodetectors 16 may be provided, and thereby, it may be designed that, when two or more kinds of light-emitting particles having different emission wavelengths are included in the sample, the light therefrom can be detected separately in accordance with the wavelengths.

The computer 18 has performs a CPU and a memory, and the inventive procedures are performed through the CPU executing various operational processings. In this regard, each procedure may be done with hardware. All or a part of processes explained in this embodiment may be performed by the computer 18 with a computer readable storage device having memorized the programs to realize those processes. Accordingly, the computer 18 may read out the program memorized in the storage device and realize the above-mentioned steps by performing the processing and calculations of information. Here, a computer readable storage device may be a magnetic disc, a magnetic optical disk, a CD-ROM, a DVD-ROM, a semiconductor memory, etc. Furthermore, the above-mentioned program may be distributed to a computer through communication line, and the computer which received this distribution may be made to execute the program.

The Principles of the Inventive Optical Analysis Technique

As described in the column of "Summary of Invention", briefly, in the inventive optical analysis technique, the intervals of generation times of signals of light-emitting particles are successively measured in time series light intensity data, and, using the signal generation time intervals measured successively, a concentration, a concentration change velocity of light-emitting particle or an index value thereof is determined in the scanning molecule counting method. In the followings, the principles of the scanning molecule counting method and the determination of a concentration, a concentration change velocity of light-emitting particle or an index value thereof, using signal generation time intervals in accordance with the present invention, will be explained.

1. Principle of Scanning Molecule Counting Method

Figure 2A:
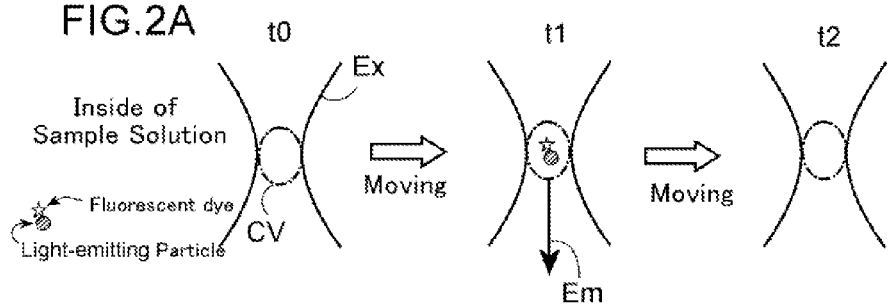
Figure 2B:
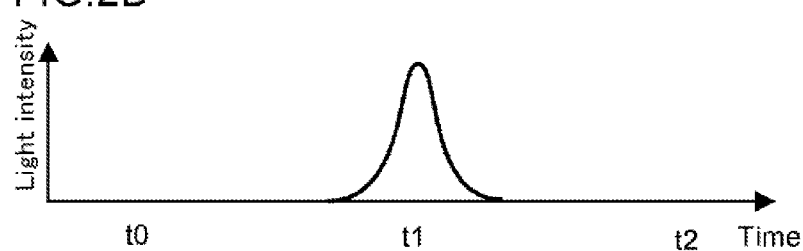

In the scanning molecule counting method (patent documents 9-12), basically, the light detection is performed together with moving the position of a light detection region CV in a sample solution, namely, scanning the inside of the sample solution with the light detection region CV by driving the mechanism for moving the position of the light detection region to change the optical path (mirror deflector 17) or by moving the horizontal position of the container 10 (micro plate 9) into which the sample solution is dispensed, as schematically drawn in FIG. 2A. Then, for example, during the moving of the light detection region CV (in the drawing, time t0-t2), when the light detection region CV passes through a region where one light-emitting particle exists (t1), light is emitted from the light-emitting particle, and a pulse form signal having significant light intensity (Em) appears on time series light intensity data as drawn in FIG. 2B. Thus, by detecting, one by one, each pulse form signal (significant light intensity) appearing as illustrated in FIG. 2B during the execution of the moving of the position of the light detection region CV and the light detection as described above, the light-emitting particles are detected individually, and by counting the number thereof, the information about the number, concentration or number density of the light-emitting particles existing in the measured region can be acquired. In the principle of the scanning molecule counting method, no statistical calculation processes, such as the calculation of the fluorescence intensity fluctuation, are conducted and the light-emitting particles are one by one detected, and therefore, the information about the concentration or number density of the particle is acquirable even in a sample solution with a low particle concentration at the level where no sufficiently accurate analysis is available in FCS, FIDA, etc.

2. Determination of Light-Emitting Particle Concentration Using Signal Generation Time Intervals As noted in conjunction with FIG. 9, in the scanning molecule counting method described in patent documents 9-12, an optical measurement is performed for a fixed measurement time or until a fixed number of particles have been detected, and a concentration value or its index value of light-emitting particles in a sample solution is computed out from the detected number in the fixed measurement time or the measurement time taken for the detection of the fixed number of particles. In this structure, in order to perform the optical measurement and the detection of a light-emitting particle concentration accurately or efficiently, it is preferable that the light-emitting particle concentration is in a quasi-static or steady state, and the concentration value of the light-emitting particles in a sample solution can be predicted at a certain degree.

Figure 2C:
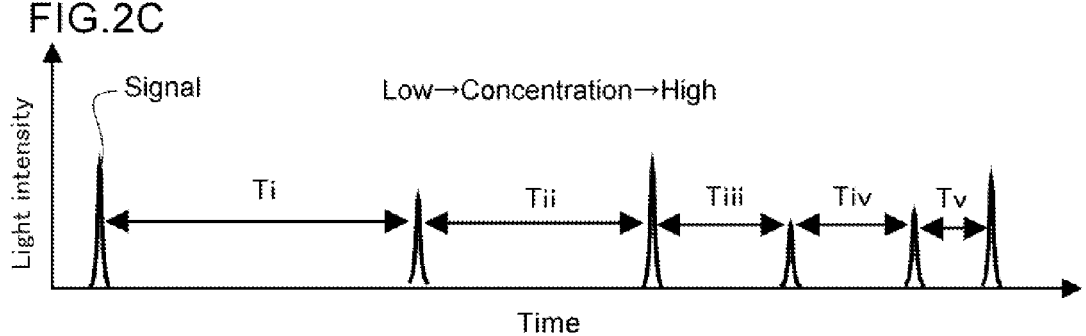

By the way, as schematically drawn in FIG. 2C, in time series light intensity data obtained by the scanning molecule counting method, as a light-emitting particle concentration is higher, the generation frequency of signals of light-emitting particles increases, and accordingly, the time interval of signal generations becomes narrower. Namely, for example, in a case that a light-emitting particle concentration increases with time, as illustrated, signal generation time intervals $T_j$ will satisfy:

$$T_i > T_{ii} > T_{iii} > T_{iv} > T_v \quad (1)$$

Figure 2D:
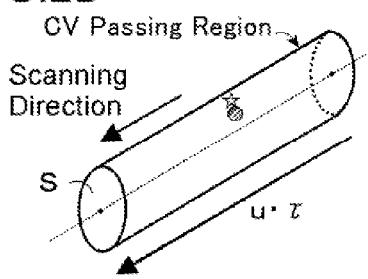

Thus, a light-emitting particle concentration can be computed out by using signal generation time intervals of light-emitting particles, and further, by tracking the signal generation time intervals successively, the change of the light-emitting particle concentration can also be tracked. Concretely, the relation between a light-emitting particle concentration and a signal generation time interval is given, as follows: As schematically drawn in FIG. 2D, when a sample solution contains light-emitting particles at a concentration C, the number P of the light-emitting particles encompassed in the light detection region CV (namely, detected) during the moving of a light detection region CV, having a cross-sectional area S in the direction perpendicular to its scanning direction, at a speed u for time $\tau$ is:

$$P = CSu\tau = C\pi r^2 u\tau \quad (2)$$

Here, the section of the light detection region CV is approximated by a circle of radius r. Accordingly, a time $\tau/P$ taken for detecting the signal of one light-emitting particle, namely, the time interval after one detection of a light-emitting particle till the detection of the next light-emitting particle (the time interval of generation of one particle), $T_j$ ($=\tau/P$), is given by:

$$T_j = 1/(C\pi r^2 u) \quad (3)$$

Thus, by measuring the signal generation time interval $T_j$, the light-emitting particle concentration C is computed by:

$$C = 1/(T_j \pi r^2 u) \quad (4)$$

In this regard, the light-emitting particle detecting process, i.e., a signal generation process, is stochastic, and thus, there are large dispersions in values of the time interval of generation of one particle. However, through successively performing the measurement of a signal generation time interval $T_j$ as shown in FIG. 2C and its conversion to the light-emitting particle concentration value and referring to the successive light-emitting particle concentration values, the dispersions in the behavior of the light-emitting particle concentration value and its time change during performing the optical measurement are cancelled at a certain degree. Moreover, the signal generation time interval may be a time interval in which a predetermined number of signals of particles have been generated. Namely, the signal generation time interval may be a time interval $T^K_j$ from the signal generation time of one particle to the signal generation time of the k-th particle, and in that case, the light-emitting particle concentration C is given by:

$$C = k/(T^K_j \pi r^2 u) \quad (4a)$$

In the case of Expression (4a), although its time resolution deteriorates, it is expected that the dispersions in the values will be suppressed. The "k" may be an integer, such as 2-50.

As noted above, according to the manner of successively measuring signal generation time intervals and computing the values of a light-emitting particle concentration, first, it becomes possible to grasp the behavior of the time variation of the light-emitting particle concentration. Thus, in a system in which a light-emitting particle concentration changes with time, it becomes possible to track the light-emitting particle concentration along time progress. Thereby, using a process of fitting to the tracked light-emitting particle concentration values, etc., it becomes possible to determine a changing velocity of the light-emitting particle concentration or a reaction velocity of a reaction related to the light-emitting particles. Such a concentration change velocity or a reaction velocity becomes useful information in an analysis or consideration with respect to the mechanism of a light-emitting particle concentration change.

Moreover, it should be understood that, according to the above-mentioned manner, because the behavior of a time variation of a light-emitting particle concentration can be grasped, there is no need to grasp a concentration level of a light-emitting particle beforehand and set a fixed measurement time or a fixed number of particle to be detected for an optical measurement. Namely, the measurement of a light-emitting particle concentration value may be performed through the processes of performing the measurement of signal generation time intervals or its conversion to a concentration value in real time during an optical measurement; monitoring the signal generation time intervals or the concentration values; and ending the optical measurement at a stage that the behavior of the time variation of the light-emitting particle concentration has been grasped at a certain degree. In this case, at a stage that the optical measurement has been conducted until the behavior of the time variation of the light-emitting particle concentration can be grasped at a certain degree, it can be judged whether the light-emitting particle concentration is in a quasi-static, steady or dynamic state, by referring to the behavior of the time variation of the light-emitting particle concentration, and thus, at that time, it is expected that the light-emitting particle concentration value can be determined with an accuracy at a certain degree even when the optical measurement is ended without waiting the completion of a fixed measurement time or the detection of a fixed number of particles. In the other words, according to the above-mentioned manner of referring to successively measured signal generation time intervals, it becomes possible to determine a light-emitting particle concentration with an accuracy at an appropriate level by the scanning molecule counting method even without grasping the level of the concentration value of the light-emitting particle or its concentration change velocity beforehand.

Furthermore, according to the above-mentioned manner, since a behavior of a time variation of a light-emitting particle concentration can be grasped, it becomes possible to estimate a light-emitting particle concentration at a time point when no optical measurement has not been performed actually. Namely, for example, a light-emitting particle concentration at a reaction start time, after enough time has passed or at a time of a reaction reaching its saturation in an arbitrary reaction can be estimated from the grasped behavior of a time variation of a light-emitting particle concentration (a concentration change velocity etc.). It should also be understood that, even when a concentration change velocity of light-emitting particle changes with time, momentary values of the light-emitting particle concentration can be estimated based on a grasped behavior of a time variation of a light-emitting particle concentration.

Operation Processes

In an embodiment of an optical analysis in accordance with the present invention with the optical analysis device 1 as illustrated in FIG. 1A, concretely, there are conducted (1) a preparation of a sample solution containing light-emitting particles; (2) processes of measuring the light intensity of the sample solution, and detecting and counting light-emitting particle signals and (3) analyses, such as a computation of a concentration and a reaction velocity coefficient, etc.

(1) Preparation of a Sample Solution

The particle to be observed in the inventive optical analysis technique may be an arbitrary particle as long as it is dispersed in a sample solution and moving at random in the solution, such as a dissolved molecule, and the particle may be, for instance, a biological molecule, i.e. a protein, a peptide, a nucleic acid, a lipid, a sugar chain, an amino acid, etc. or an aggregate thereof, a virus, a cell, a metallic colloid or other non-biological particles (Typically, the sample solution is an aqueous solution, but not limited to this, and it may be an organic solvent or other arbitrary liquids.). Further, the particle to be observed may be a particle which emits light by itself or a particle to which a light emitting label (a fluorescence molecule, a phosphorescence molecule, and a chemiluminescent or bioluminescent molecule) is attached in an arbitrary manner. Moreover, in the present invention, since the tracking of a behavior of a time variation of a light-emitting particle concentration is possible, for example, a light-emitting particle of which the concentration changes owing to a binding/dissociation reaction or an intermolecular interaction, or a light-emitting particle of which the light-emitting characteristic changes owing to a structural change can be used as a particle to be observed.

Figure 3A:
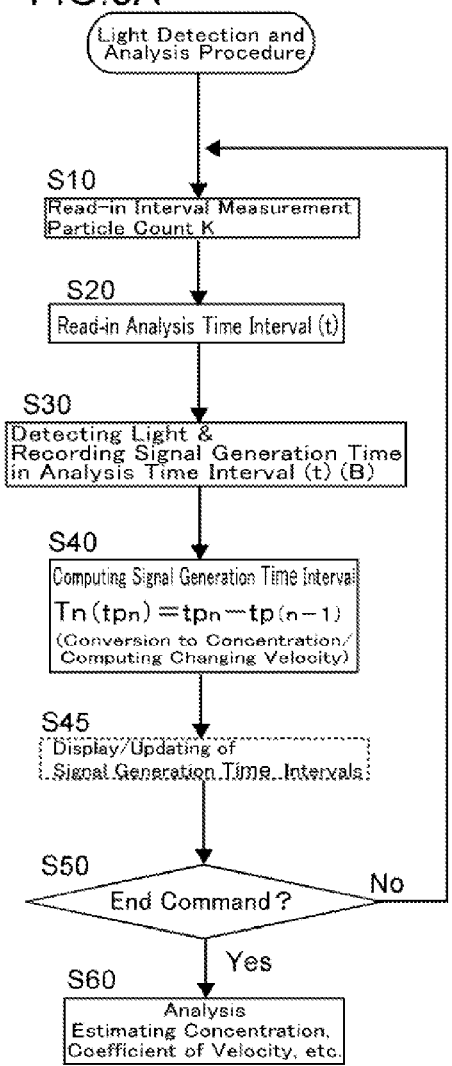
Figure 3B:
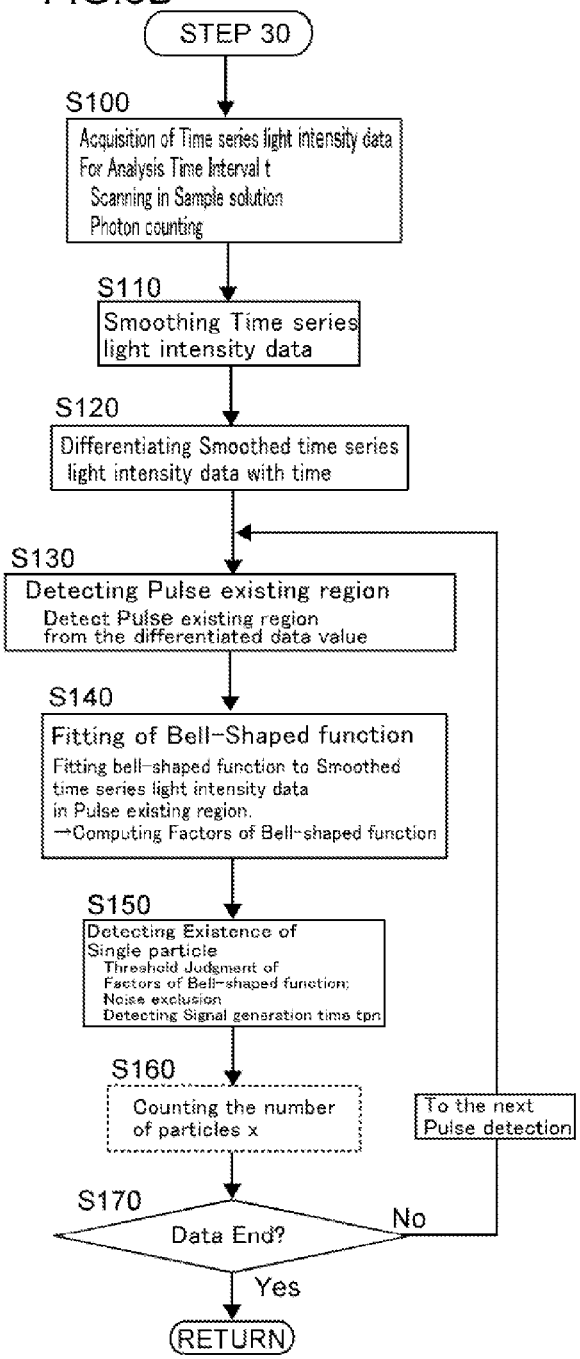

(2) Measurement of Light Intensity of a Sample Solution and Detection of a Light-Emitting Particle FIGS. 3A-3B shows in the form of flow chart one example of processes for measuring a light intensity of a sample solution, detecting light-emitting particles and measuring signal generation time intervals in the present embodiment performed using the optical analysis device 1 illustrated in FIG. 1A. In the illustrated example, briefly, a series of processes of moving the position of a light detection region, detecting light from the light detection region and detecting signals from light-emitting particles are performed by an analysis time interval t, arbitrarily set (comparatively short), and when a signal of a light-emitting particle is detected, the measurement of the time interval between its time and the time of the previous detection of a signal of a light-emitting particle (signal generation time interval Tn or $T^K n$) is performed, and preferably, the signal generation time interval Tn, $T^K n$, or a light-emitting particle concentration value converted from the signal generation time interval, or its index value are displayed in real time. And, these processes are continuously performed for arbitrary time repeatedly. In this regard, it should be understood that a series of processes and structures, described below, are realized by the processing operation of the computer 18.

(i) Initial Setting

Referring to FIG. 3A, in concrete operation processes, first, after dispensing a sample solution into the well(s) 10 of the micro plate 9 and putting it on the stage of the microscope, when a user inputs to the computer 18 a command of starting the measurement of light intensity, detection of light-emitting particles, and measurement of signal generation time intervals, the computer 18 executes the read-in of a particle count referred to in a measurement of a signal generation time interval [interval measurement particle count K] (step 10) and an analysis time interval t (step 20). The interval measurement particle count K may be an arbitrary integer more than zero. The analysis time interval t may be set to an arbitrary time sufficiently longer than a length of a signal of one light-emitting particle (>2r/u) preferably, taking into account a moving speed (u) and size (2r) of a light detection region (This is for avoiding, as much as possible, that a signal of one light-emitting particle appears across two or more analysis time intervals t.). The interval measurement particle count K and analysis time interval t may be values inputted by the user or appropriately set in the computer 18 in an arbitrary manner.

(ii) Detection of the Number of Light-Emitting Particles

Then, when the interval measurement particle count K and the analysis time interval t have been read-in, it is repeated by the analysis time interval t to execute processes of measuring light intensity by the scanning molecule counting method for the analysis time interval t, detecting signals of light-emitting particles from the measured light intensity data and recording signal generation times (step 30) and a process of computing generation time intervals of the light-emitting particle signals detected in step 30 (step 40) as described below. In this regard, preferably, the signal generation time intervals computed in step 40 and light-emitting particle concentration values or its index value obtained by converting the signal generation time intervals may be shown in real time in a manner that their changes with time progress can be visually recognized by the user (for example, a graphical representation, etc. showing the changes with time) on the display of the computer 18 (step 45). In the followings, the processes of steps 30-45 are explained in detail.

(a) Measurement of Light Intensity

FIG. 3B shows an example of the process in step 30 in the form of flow chart. Referring to this drawing, in the process in step 30, first, the measurement of light intensity for the analysis time interval t while moving the position of the light detection region within the sample solution (scanning in the sample solution) by driving the mirror deflector 17 or the stage position changing apparatus 17a (step 100). In this process, typically, the radiating of excitation light (only when needed) into the light detection region in the sample solution and the measuring of the light intensity in the light detection region are started in accordance with programs (a procedure of moving the position of the light detection region in the sample solution, a procedure of irradiating a light detection region with excitation light (only when needed) and a procedure of detecting the light from the light detection region during moving the position of the light detection region) memorized in a memory device (not shown). When the measurement is started, first, under the operational control of the computer 18 according to the program, the light of an excitation wave length of the light-emitting particle in the sample solution is emitted from the light source 2 while the moving of the position of the light detection region in the well 10 is performed by driving the mirror 7 (galvanometer mirror) by the mirror deflector 17, or driving the stage by the stage position changing apparatus 17a, and simultaneously with these, the photodetector 16 successively converts the received light into electrical signals and transmits them to the computer 18 while the computer 18 generates and saves time series light intensity data from the transmitted signals in an arbitrary manner. Typically, the photodetector 16 is a super-high sensitive photodetector which can detect an arrival of a single photon, and thus, the detection of light may be conducted by photon counting, successively performed in a manner that the number of photons arriving at the photodetector is measured in each predetermined unit time (BIN TIME), for example, in each 10 μseconds, and the time series light intensity data may be time series photon count data.

Figure 4A:
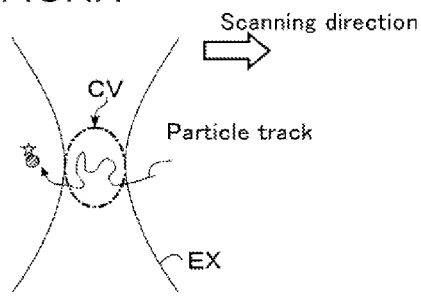

With respect to the moving speed of the position of the light detection region, in the scanning molecule counting method, in order to perform quantitatively precisely individual detection of a light-emitting particle to be observed from the measured time series light intensity data, preferably, the moving speed of the position of the light detection region during light intensity measurement is set to a value quicker than the moving speed in the random motion, i.e., the Brownian motion of the light-emitting particle. When the moving speed of the position of the light detection region is slower than the movement of a particle owing to the Brownian motion, the particle moves at random in the region as schematically drawn in FIG. 4A, whereby the light intensity changes at random (the excitation light intensity in the light detection region is reduced outwardly from the peak at the center of the region), so that it would become difficult to determine a significant light intensity change corresponding to each light-emitting particle (a signal indicating light from a light-emitting particle). Then, preferably, as drawn in FIG. 4B, the moving speed of the position of the light detection region is set to be quicker than the average moving speed of a particle by the Brownian motion (diffusional moving velocity), so that the particle will cross the light detection region CV in an approximately straight line and thereby the profile of the change of the light intensity corresponding to each particle will become approximately bell shaped similarly to the excitation light intensity distribution as illustrated in FIG. 4C the most upper row, and thus, the correspondence between each light-emitting particle and light intensity can be easily determined.

Concretely, the time $\Delta\tau$ required for a light-emitting particle having a diffusion coefficient D to pass through the light detection region of radius r (confocal volume) by the Brownian motion is given from the equation of the relation of mean-square displacement:

$$(2r)^2 = 6D \cdot \Delta\tau \qquad (5)$$

as:

$$\Delta\tau = (2r)^2/6D \qquad (6),$$

and thus, the velocity of the light-emitting particle moving by the Brownian motion (diffusional moving velocity) Vdif, becomes approximately $$V\mathrm{dif} = 2r/\Delta\tau = 3D/r \qquad (7)$$

Then, with reference to this, the moving speed of the position of the light detection region may be set to a value sufficiently quicker than Vdif. For example, when the diffusion coefficient of a light-emitting particle is expected to be about $D = 2.0 \times 10^{-10}$ m$^2$/s, Vdif will be $1.0 \times 10^{-3}$ m/s, supposing r is about 0.62 μm, and therefore, the moving speed of the position of the light detection region may be set to its 10 times or more, e.g., 15 mm/s. In this regard, when the diffusion coefficient of a light-emitting particle is unknown, an appropriate moving speed of the position of the light detection region may be determined by repeating the executions of a preliminary experiment with setting various moving speeds of the position of the light detection region in order to find the condition that the profile of the light intensity variation becomes an expected profile (typically, similar to the excitation light intensity distribution).

(b) Detection of a Signal Corresponding to a Light-Emitting Particle

When the time series light intensity data of light-emitting particles in the sample solution in the analysis time interval t is obtained through the above-mentioned processes, the detection of a signal corresponding to light from a light-emitting particle on the light intensity data is performed through processes according to the program memorized in the memory device in the computer 18.

Figure 4B:
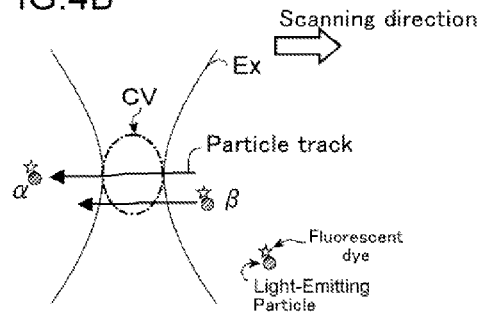
Figure 4C:
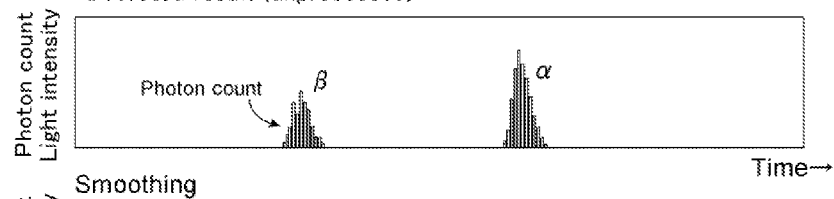
Figure 4C:
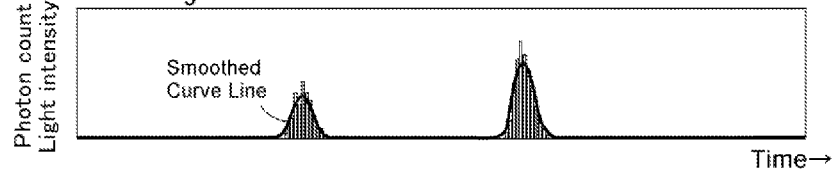
Figure 4C:
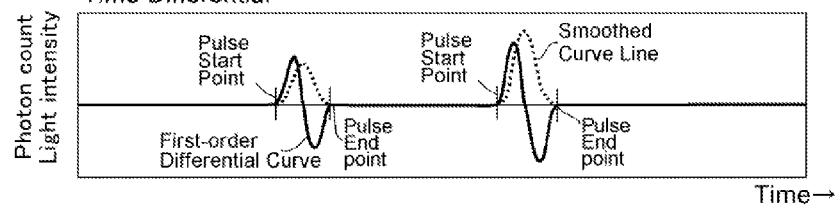
Figure 4C:
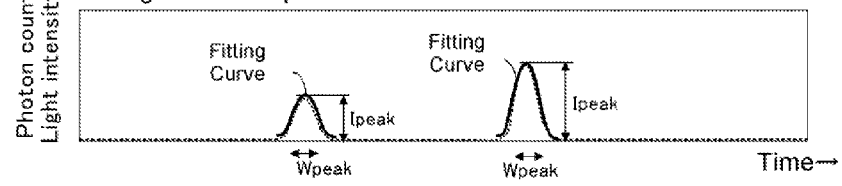

In time series light intensity data, when the track of one light-emitting particle in its passing through the light detection region is approximately straight as shown in FIG. 4B, the light intensity variation in the signal corresponding to the particle has a bell shaped profile reflecting the light intensity distribution in the light detection region (determined by the optical system) (see FIG. 4C, the most upper row). Thus, basically in the scanning molecule counting method, when the time width for which the light intensity value exceeding an appropriately set threshold value continues is in a predetermined range, the signal having the profile of the light intensity may be judged to correspond to one particle having passed through the light detection region, and thereby one light-emitting particle is detected. And a signal, of which the time width for which the light intensity exceeding the threshold value continues is not within the predetermined range, is judged as noise or a signal of a contaminant. Further, when the light intensity distribution in the light detection region can be assumed as a Gaussian distribution:

$$I = A \cdot \exp(-2t^2/a^2) \quad (8),$$

and when the intensity A and the width a, computed by fitting Expression (8) to the profile of a significant light intensity (a profile which can be clearly judged not to be a background), are within the respective predetermined ranges, the profile of the light intensity may be judged to correspond to one particle having passed through the light detection region, and thereby the detection of one light-emitting particle will be done (The signal with the intensity A and the width a out of the predetermined ranges may be judged as a noise or a contaminant signal and ignored in the later analysis, etc.).

As one example of more concrete ways for the processes of detection of (a) signal(s) from the time series light intensity data, first, a smoothing treatment is performed to the time series light intensity data (FIG. 4C, the most upper row "detected result (unprocessed)") (FIG. 3B—step 110, FIG. 4C mid-upper row "smoothing"). Although the light emitted by a light-emitting particle is stochastic so that minute time gaps will be generated in data values, such gaps in the data values can be disregarded by the smoothing treatment. The smoothing treatment may be done, for example, by the moving average method, etc. In this regard, parameters in performing the smoothing treatment, e.g., the number of datum points in one time of the averaging, the number of times of moving average executions, etc. in the moving averages method, may be appropriately set in accordance with the moving speed (scanning speed) of the position of the light detection region and/or BIN TIME in the light intensity data acquisition.

Next, on the time series light intensity data after the smoothing treatment, in order to detect a time domain (pulse existing region) in which a significant pulse form signal (referred to as "pulse signal" hereafter) exists, the first differentiation value with time of the smoothed time series light intensity data is computed (step 120). As illustrated in FIG. 4C, the mid-low row "time differential", in the time differential value of time series light intensity data, the value variation increases at the time of the signal value change, and thereby, the start point and the end point of a significant signal can be determined advantageously by referring to the time differential value.

Figure 5:
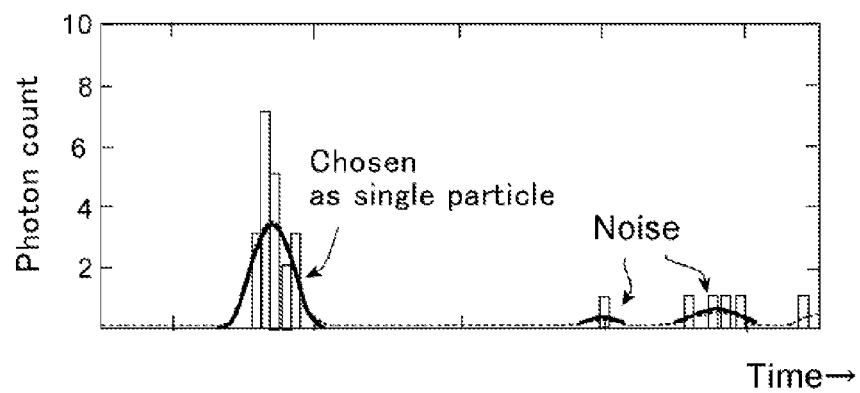
FIG. 5 shows examples of measured photon count data (bar graph); curves obtained by carrying out the smoothing of the data (dotted line); and Gauss functions fitted on the pulse existing region (solid line). In the drawing, the signals attached with "noise" are disregarded as signals due to noises or contaminants.

After that, significant pulse signals are detected sequentially on the time light intensity data and it is judged whether or not the detected signal is a signal corresponding to a light-emitting particle. Concretely, first, on the time series time-differential value data of the time series light intensity data, the start point and the end point of one pulse signal are searched and determined by referring to the time differential value sequentially, so that a pulse existing region will be specified (step 130). When one pulse existing region has been specified, the fitting of a bell-shaped function is applied to the smoothed time series light intensity data in the pulse existing region (FIG. 4C, the lower row "bell-shaped function fitting"), and then, parameters of the pulse of the bell-shaped function, such as the peak intensity (the maximum), Ipeak; the pulse width (full width at half maximum), Wpeak; the correlation coefficient in the fitting (of the least square method), etc. are computed (step 140). In this regard, although the bell-shaped function to be used in the fitting is typically a Gauss function as in Expression (8), it may be a Lorentz type function. Then, it is judged whether or not the computed parameters of the bell shaped function are within the respective ranges assumed for the parameters of the bell-shaped profile drawn by a pulse signal to be detected when one light-emitting particle passes through the light detection region, namely, whether or not the peak intensity, pulse width and correlation coefficient of a pulse are in the respective predetermined ranges, etc. (Step 150). Accordingly, the signal, whose computed parameters of the bell-shaped function are judged to be within the ranges assumed in a light signal corresponding to one light-emitting particle, as shown in FIG. 5 left, is judged as a signal corresponding to one light-emitting particle, and thereby one light-emitting particle has been detected and the generation time tpn of this signal (e.g. the time of the peak) is detected and recorded. On the other hand, a pulse signal, whose computed parameters of the bell-shaped function are not within the assumed ranges, as shown in FIG. 5 right, is disregarded as noise. Moreover, since two or more light-emitting particle signals can be generated on the time series light intensity data in one analysis time interval t, the number of the detected signals of light-emitting particles may be counted (step 160).

The searching and judging of a pulse signal and recording of its generation time in the above-mentioned processes of steps 130-160 are repetitively carried out throughout light intensity data for the analysis time interval t. (step 170). In this connection, the processes for detecting individually a signal from the time series light intensity data may be performed by an arbitrary way, other than the above-mentioned procedures. When the searching of pulse signals in all the time series light intensity data for the analysis time interval t is completed, step 30 is ended and step 40 is performed.

(iii) Computation of Signal Generation Time Intervals (and Display and Updating)

Thus, when the process of detecting light-emitting particle signals in time series light intensity data for an analysis time interval t has been done, generation time intervals Tn of the detected signals are computed. With respect to the signal generation time interval Tn, when the interval measurement particle count is K=1, the difference $tp_n - tp_{(n-1)}$ between the generation time tpn of the light-emitting particle signal detected in the last step 30 and the light-emitting particle signal generation time tp(n−1) detected previously is computed as Tn ($tp_n$). In this regard, in one measurement, for the first detected light-emitting particle signal, no signal generation time interval Tn needs to be computed. Further, when two or more light-emitting particle signals have been detected in the analysis time interval t of the last step 30, for each light-emitting particle signal, the light-emitting particle signal generation time measured from the generation time of the light-emitting particle signal having been generated just before the each light-emitting particle signal is computed.

When the interval measurement particle count is K>1, for the signal generation time interval Tn, a signal generation time interval $T^K n$ may be computed each time when the number of detected light-emitting particle signals reaches K. Namely, when the Kth signal occurs from the generation of the first detected light-emitting particle signal or the generation of the signal for which the signal generation time interval $T^K n$ has been computed, the difference between its generation time $tp_n$ and the generation time of the first detected light-emitting particle signal or the signal for which the signal generation time interval has been computed, $tp_{(n-1)}$, is computed as the signal generation time interval $T^K n$.

When the signal generation time interval Tn or $T^K n$ is computed as noted above, this value may be displayed on the display of the computer 18 as already noted. Although it is preferable that the display is shown in a graph form where the horizontal axis indicates the lapsed time from the measurement start while the ordinate axis indicates the signal generation time interval such that the time variation of the signal generation time interval can be grasped easily, the way of the displaying is not limited thereto. Furthermore, the value obtained by converting the signal generation time interval into the light-emitting particle concentration C or an arbitrary index value which enables the grasping of the time variation of the light-emitting particle concentration C (e.g., the reciprocal of the signal generation time interval, etc.), using Expression (4) or (4a), may be displayed in a graph form.

(d) End of Measurement

As already noted, the processes in steps 10-45 may be repeatedly performed by the analysis time interval t over an arbitrary time. In this respect, the measurement of the light intensity in step 100 of FIG. 3B is, preferably, performed continuously from the start of the measurement to its end even during the execution of signal processing steps other than step 100. Namely, in the processing cycle of FIG. 3, when one cycle of a measurement of the light intensity of step 100 for the analysis time interval t is completed, the next cycle of the measurement of the light intensity of step 100 for the analysis time interval t is performed continuously, and simultaneously with this, the processes of detecting a signal of a light-emitting particle and determining a signal generation time interval from the light intensity data acquired for the analysis time interval t in the completed cycle are executed in the computer 18. According to this, the detection of light-emitting particles and the determination of signal generation time intervals are achieved in real time.

As noted above, according to the manner that the signal generation time intervals and the time variation of a light-emitting particle concentration can be grasped in real time during the light measurement, the interval measurement particle count K and the analysis time interval t may be changed appropriately with reference to the time variation. Also, the series of processes may be ended at an arbitrary time. If a time variation of the signal generation time intervals or the light-emitting particle concentration can be grasped in real time during the light measurement, the user may command the end of the measurement to the device 1 at an arbitrary time with reference to the time variation, and, thereby, the measurement may be ended (step 50). On the other hand, when the user does not give a command of ending the measurement, the measurement ends automatically after a fixed time has passed or after the detected number of signals reaches a constant value. It should be understood that, in the present invention, since the time variation of a light-emitting particle concentration will be observed, the measurement may be ended at a time when a result enabling the grasping of the dynamic behavior of the change of the light-emitting particle concentration is obtained.

(3) Analyses, Such as Computation of Concentration Value or Concentration Changing Velocity Value, Etc.

As noted above, since a time variation of a light-emitting particle concentration will be observed by measuring signal generation time intervals with time progress during a light measurement, a concentration change velocity is computable from the measuring result. Since a manner of a time variation of a light-emitting particle concentration differs depending upon mechanisms of phenomena (a structural change, a binding and dissociation reaction, etc.) relating to a light-emitting particle, a concentration changing velocity value, a changing velocity coefficient, etc. can be computed through fitting a model formula anticipated from an appropriately selected mechanism to the time variation of the observed light-emitting particle concentration (an equation of a concentration value, which is a function of time, etc.). Moreover, when a mechanism of a phenomenon related to a light-emitting particle consistent with a time variation of an observed light-emitting particle concentration is found out, a light-emitting particle concentration value and/or a concentration changing velocity value at a time region in which no optical measurement has been conducted can be estimated. Furthermore, since the signal generation time interval will not change substantially when a light-emitting particle concentration change is in a quasi-static or steady state, it is expected that a light-emitting particle concentration value can be determined with sufficient accuracy from the average value of signal generation time intervals during the optical measurement having been performed or the average value of concentration values obtained by converting the signal generation time intervals.

By the way, in Expression (4) or (4a), which converts a signal generation time interval to a light-emitting particle concentration, the cross-sectional radius r of the region through which the light detection region has passed may be theoretically computed out with the wavelength of excitation light or detected light, the numerical aperture of lenses and the adjustment condition of the optical system, or may be determined experimentally, for instance, using the number of light-emitting particles detected as explained above by performing light intensity measurement, detection of (a) light-emitting particle(s) and their counting with a solution having a known light-emitting particle concentration (a reference solution) under the same condition as the measurement of a sample solution to be tested, and the light-emitting particle concentration of the reference solution. Concretely, for example, supposing the number of detected light-emitting particles is N in a light intensity measurement performed at a moving speed uo for a certain time to with a reference solution of a light-emitting particle concentration C, the cross-sectional area S of the region through which the light detection region has passed is given by:

$$S = N/(C \cdot N_A \cdot uo \cdot to) \quad (9)$$

(Here, $N_A$ is Avogadro's number.). Alternatively, by preparing the plurality of solutions of different light-emitting particle concentrations and performing the measurement for each of the solutions, the average value of the computed Ss may be employed as the cross-sectional area S of the light detection region. In this regard, the cross-sectional area S of the light detection region may be given by an arbitrary method, for instance, using FCS and FIDA, instead of the above-mentioned method. Further, in the optical analysis device of this embodiment, there may be previously memorized in a storage device of the computer 18 the information on the relations (Expression (9)) between concentrations C and light-emitting particle numbers N of various standard light-emitting particles for assumed moving patterns of the light detection region, so that a user of the device can appropriately use the memorized information on the relation in conducting an optical analysis.

In order to verify the validity of the present invention explained above, the experiments described below were conducted. In this regard, it should be understood that the following embodiments illustrate the validity of the present invention only, not intended to limit the scope of the present invention.

Embodiment 1

The scanning molecule counting method was performed using, as a particle to be observed, a nucleic acid attached with a light emitting label, which was designed such that its emitted light intensity was increased with a digestive reaction by enzyme, and it was verified that the time variation of the concentration of the light-emitting particle (the nucleic acid molecule of which the emitted light intensity increased) could be tracked with reference to the signal generation time intervals.

Figure 6:
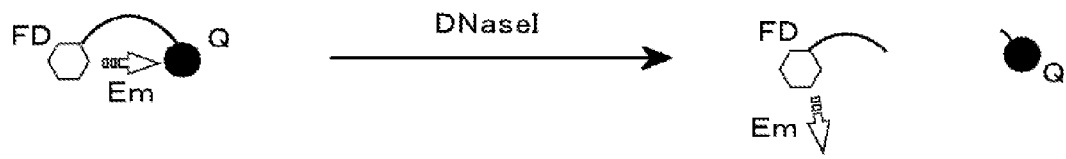
FIG. 6 is a drawing of a model of a reaction of light-emitting particles used in Embodiment 1.

The sample solution was prepared by dissolving, as a particle to be observed, poly-T of five bases, in which a fluorescent dye, ATTO647N, was attached to the 5'-end and a quenching molecule, BHQ3, was attached to the 3'-end, at 10 pM in a reaction buffer (40 mM Tris-HCl pH 7.5, 8 mM MgCl2, 5 mM DTT). The poly-T has a base sequence: ATTO647 N-TTTTT-BHQ3, and in this particle, under an unreacted condition, the light Em emitted from ATTO647N (FD) is absorbed by BHQ3 (Q) as schematically drawn in FIG. 6 left, and thus, no substantial light is emitted outside; while, when the base chain is cut by a DNA digestive enzyme (DNaseI), the light Em emitted from ATTO647N will be emitted outside without being absorbed as schematically drawn in FIG. 6 right, and thereby the particle becomes observable as a light-emitting particle. In this regard, poly-T was synthesized by requesting Sigma Genosis, Inc.

In the measurement, a single molecule fluorescence measuring apparatus MF20 (Olympus Corporation), equipped with the optical system of a confocal fluorescence microscope and a photon counting system, was used as the optical analysis device, and 40U of DNaseI (TAKARA Co., Ltd.) was added to 36 μL of the above-mentioned sample solution, and the solution was quickly agitated, and then, the light intensity measurement was started in accordance with the scanning molecule counting method as mentioned above. In the light intensity measurement, 642 nm laser light (1 mW output) was used for the excitation light, and the detected light wavelength band was set to 660-710 nm using a band pass filter. The light detection region in the sample solution was moved at 69 mm/s of scanning speed along a circular track by the mirror deflector. Further, BIN TIME in the photon counting was 10 μseconds.

Furthermore, in the process of detecting signals of light-emitting particles in the time series photon count data acquired by the light intensity measurement, first, a smoothing process was conducted (the process of making a moving average with 13 data points in accordance with Savisky-Golay method were repeated 5 times.), and, using the first differential values of the smoothed data, regions where a pulse signal exists (pulse existing region) were specified. Then, a Gauss function was fit to each specified pulse existing region with the least-squares method, and the peak intensity, pulse width (full width at half maximum) and correlation coefficient (in the Gauss function) were determined, and then, a pulse signal which satisfied the following conditions:

20 μsecond<pulse width<200 μsecond

Peak intensity>1(photon/10 μsecond)

Correlation coefficient>0.95 was judged as a signal having the characteristics of a signal of a light-emitting particle.

Figure 7A:
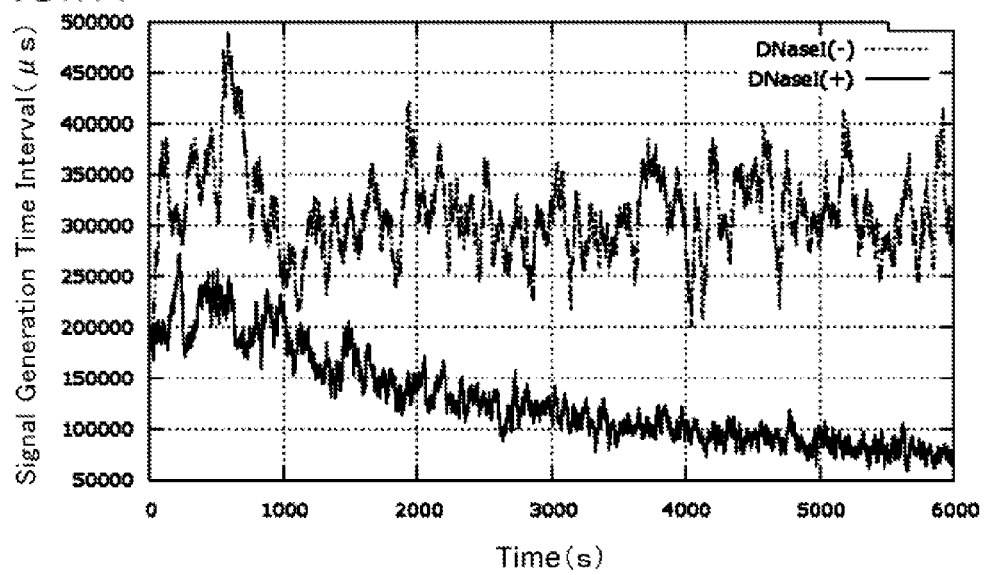
FIG. 7A shows a time variation of the generation time interval of light-emitting particle signals (the time interval of generation of one particle) obtained in Embodiment 1.
Figure 7B:
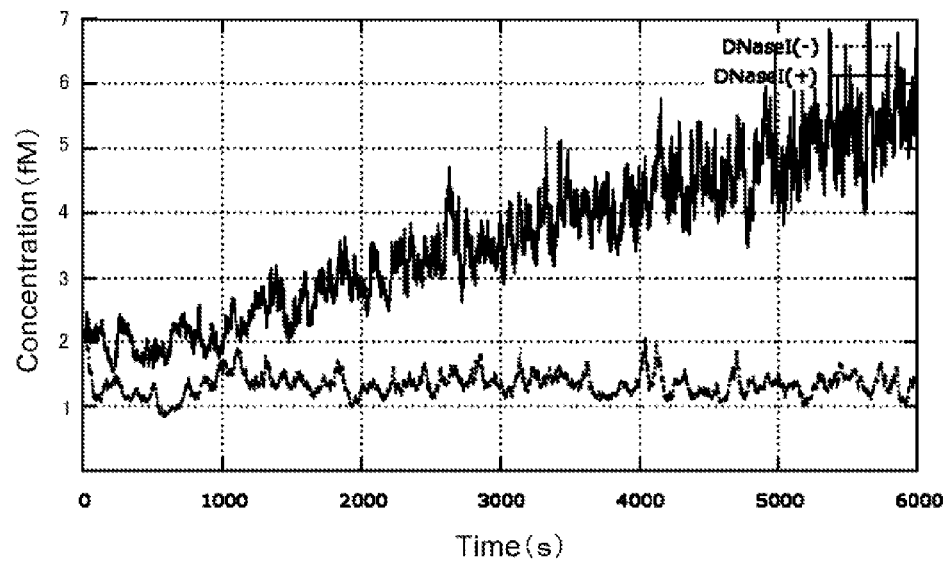
FIG. 7B shows a time variation of a light-emitting particle concentration converted from the generation time intervals of the light-emitting particle signals.

FIG. 7A and FIG. 8A each are graphs in which signal generation time intervals of light-emitting particles detected on the time series light intensity data in the above-mentioned way were plotted against the lapsed time after a measurement start. FIG. 7A shows the signal generation time intervals by one particle (K=1), and FIG. 8A shows the signal generation time intervals by 50 particles (K=50). In the drawings, there are shown signal generation time intervals in a case that DNaseI was added (DNaseI+) and in a case that DNaseI was not added (DNaseI−). In this regard, in the illustrated experiment, in the case that DNaseI was added (DNaseI+), the time taken for the agitation from the addition of DNaseI was about 15 seconds. Further, FIG. 7B and FIG. 8B show the time variations of the light-emitting particle concentration value calculated from the signal generation time intervals in FIG. 7A and FIG. 8A, using Expression (4) and (4a), respectively.

As understood with reference to FIG. 7A and FIG. 8A, in the case that DNaseI was not added (DNaseI−), although the fluctuation of the signal generation time interval was large, no tendency for its time length to change in one direction with time progress was not observed. On the other hand, in the case that DNaseI was added (DNaseI+), although the signal generation time interval was 0.2 to 0.25 seconds just after the measurement start, the tendency of the signal generation time interval to decrease gradually with time progress was observed (at 6000 seconds after the measurement start, the signal generation time interval was about 0.07 second). Moreover, as understood from FIG. 7B and FIG. 8B, while no substantial change in the light-emitting particle concentration value was seen when DNaseI was not added (DNaseI−), a significant increase in the light-emitting particle concentration value was observed when DNaseI was added (DNaseI+), corresponding to the time variation of the signal generation time interval. These results show that poly-T was cut by digestion of DNaseI, and thus, the fluorescent dye, ATTO647N, and the quenching molecule, BHQ3, were separated mutually, and thereby, the light of the fluorescent dye ATTO647N became emitted outside without being absorbed as explained in relation to FIG. 6, and that the digestive reaction of DNaseI progressed with time progress, and thus, the concentration of the detectable poly-T (light-emitting particle) was increased. That is, in accordance with the teachings of the present invention, it was shown that a light-emitting particle concentration change can be observed with reference to signal generation time intervals of light-emitting particles detected on time series light intensity data obtained by the scanning molecule counting method. Furthermore, comparing the graphs in FIGS. 7A, 7B and FIGS. 8A, 8B, it is observed that the dispersions in values in the latter are smaller than in the former. This indicates that, in the measuring signal generation time intervals, the dispersion in the values can be suppressed by rendering a signal generation time interval to be an interval of generation times of several number of signals at a degree that the time variation of the signal generation time interval can be grasped.

Furthermore, using the above-mentioned result (FIG. 8B), it was verified whether or not the time variation of the measured light-emitting particle concentration value was consistent with the mechanism of the digestive reaction of the nucleic acid by DNaseI. In the digestive reaction of the nucleic acid by DNaseI, DNaseI concentration (enzyme concentration) [E], nucleic acid concentration (substrate concentration) [S], DNaseI-nucleic acid conjugate concentration [ES], and reaction product concentration [P] are considered to follow the equation:

$$[E]+[S]<->[ES]->[P] \quad (10)$$

In this reaction equation, it is considered that the reaction velocity at which a DNaseI-nucleic acid conjugate changes to the reaction product is given by:

$$d[P]/dt=k[ES] \quad (11)$$

and, [P] is given by:

$$[P]=k[ES]t+C$$

Here, t is lapsed time, k is a reaction velocity coefficient, and C is a constant of integration (initial concentration of a reaction product). In this regard, in the condition of this experiment, the DNaseI-nucleic acid conjugate concentration [ES] was high enough so that it could be considered that [ES] remained unchanged, and therefore, d[P]/dt was substantially constant, and the reaction product concentration [P], i.e., the light-emitting particle concentration detected can be approximated linearly by:

$$[P]=vt+C \quad (12)$$

(v is the concentration change velocity.).

Then, when the fitting of Expression (12) to the result of FIG. 8B was carried out, the time variation of the measured light-emitting particle concentration was almost in agreement with Expression (12) as shown by the straight line FL in the drawing, and the approximate straight lines became as follows, respectively:

$$\text{DNaseI--: } [P]=2.99+2.27\times10^{*5}t$$

$$\text{DNaseI+: } [P]=3.44+0.00129t$$

Namely, it was observed that the digestive reaction velocity by DNaseI was 0.00129 [fM/s], and when there was no addition of DNaseI, there was no substantial concentration change. This result strongly suggests that the light-emitting particle concentration value in this experiment was consistent to the concentration value given by Expression (12), and the detected signals were signals indicating light of the light-emitting particles. In addition, in the conditions of this experiment, the amount of DNaseI was higher as compared with the nucleic acid, and thus [ES] was considered to be substantially equal to $[S]_0$: the initial concentration of [S], and therefore, [P] is given by:

$$[P]=k[ES]t+C=k[S]_0t+C \quad (13)$$

Therefore, if the initial concentration $[S]_0$ is known, the coefficient of velocity k can be computed by computing out a reaction velocity (concentration change velocity). On the other hand, when the coefficient of velocity k is known, a substrate initial concentration $[S]_0$ can be computed. Furthermore, it should be understood that, when the mechanism of a reaction in agreement with an experiment has been confirmed as noted above, a light-emitting particle concentration at a time when no optical measurement has been actually performed can also be estimated from the above-mentioned equation (11) or (13).

Thus, as understood from the result of the above-mentioned embodiment, it has been shown that, in accordance with the teachings of the present invention, the time variation of a light-emitting particle concentration can be tracked by measuring signal generation time intervals successively in the scanning molecule counting method, and thereby, even for a system in which a light-emitting particle concentration changes with time, i.e., the light-emitting particle concentration is in a dynamic state, the value of the light-emitting particle concentration or its index value can be estimated, and it is possible to detect the concentration change velocity of a light-emitting particle or a reaction velocity of a reaction related to a light-emitting particle. Moreover, in a case that a light-emitting particle concentration is in a quasi-static or steady state, even when an approximate value of the light-emitting particle concentration is unknown, if it is judged that the light-emitting particle concentration is in a quasi-static or steady state by referring to the time variation of signal generation time intervals, the light-emitting particle concentration value can be detected with sufficient accuracy in a comparatively wide range even when no estimated value of the light-emitting particle concentration has been obtained beforehand.

The invention claimed is:

1. An optical analysis device which detects light from light-emitting particles dispersed and moving at random in a sample solution using an optical system of a confocal microscope or a multiphoton microscope, comprising:
    a light detection region mover which moves a position of a light detection region of the optical system in the sample solution;
    a light detector which detects light from the light detection region; and
    a signal processor which generates time series light intensity data of the light from the light detection region detected with the light detector during the moving of the position of the light detection region in the sample solution and detects each of signals of the light-emitting particles individually in the time series light intensity data;
    wherein the signal processor measures successively an interval of generation times between the signals of individual light-emitting particles detected in the time series light intensity data one-by-one along time progress of the time series light intensity data, and determines an index value representing a concentration of the light-emitting particles using a plurality of the signal generation time intervals measured successively, and
    wherein an increase in the interval of generation times between the signals of the individual light-emitting particles detected in the time series light intensity data one-by-one along time progress of the time series light intensity data corresponds to a decrease in the concentration of the light-emitting particles, and vice versa.

2. The device of claim 1, wherein the signal processor determines an index value representing a changing velocity of the concentration of the light-emitting particles using the plurality of the successively measured signal generation time intervals.

3. The device of claim 1, wherein the signal processor determines an index value representing the concentration of the light-emitting particles at an arbitrary time using the plurality of the successively measured signal generation time intervals.

4. The device of claim 1, wherein the interval of the generation times of the signals of the light-emitting particles is a time interval in which a predetermined number of the signals of the light-emitting particles have been generated.

5. An optical analysis method of detecting light from light-emitting particles dispersed and moving at random in a sample solution using an optical system of a confocal microscope or a multiphoton microscope, comprising:
  (a) moving a position of a light detection region of the optical system in the sample solution;
  (b) measuring a light intensity from the light detection region during the moving of the position of the light detection region in the sample solution to generate time series light intensity data;
  (c) detecting individually signals of the light-emitting particles in the time series light intensity data;
  (d) measuring successively an interval of generation times between the signals of individual light-emitting particles detected in the time series light intensity data one-by-one along time progress of the time series light intensity data; and
  (e) determining an index value representing a concentration of the light-emitting particles using a plurality of the signal generation time intervals measured successively, using a signal processor,
  wherein an increase in the interval of generation times between the signals of the individual light-emitting particles detected in the time series light intensity data one-by-one along time progress of the time series light intensity data corresponds to a decrease in the concentration of the light-emitting particles, and vice versa.

6. The method of claim 5, further comprising: (f) determining an index value representing a changing velocity of the concentration of the light-emitting particles using the plurality of the successively measured signal generation time intervals, using the signal processor.

7. The method of claim 5, wherein, in the step (e), an index value representing the concentration of the light-emitting particles at an arbitrary time is determined using the plurality of the successively measured signal generation time intervals, using the signal processor.

8. The method of claim 5, wherein the interval of the generation times of the signals of the light-emitting particles is a time interval in which a predetermined number of the signals of the light-emitting particles have been generated.

9. A non-transitory computer readable storage device having a computer program product including programmed instructions for optical analysis of detecting light from light-emitting particles dispersed and moving at random in a sample solution using an optical system of a confocal microscope or a multiphoton microscope, said programmed instructions causing a computer to perform steps of:
  moving a position of a light detection region of the optical system in the sample solution;
  measuring a light intensity from the light detection region during the moving of the position of the light detection region in the sample solution to generate time series light intensity data;
  detecting individually signals of the light-emitting particles in the time series light intensity data;
  measuring successively an interval of generation times between the signals of individual light-emitting particles detected in the time series light intensity data one-by-one along time progress of the time series light intensity data; and
  determining an index value representing a concentration of the light-emitting particles using a plurality of the signal generation time intervals measured successively,
  wherein an increase in the interval of generation times between the signals of the individual light-emitting particles detected in the time series light intensity data one-by-one along time progress of the time series light intensity data corresponds to a decrease in the concentration of the light-emitting particles, and vice versa.

10. The non-transitory computer readable storage device of claim 9, said programmed instructions causing a computer to further perform step: computing out an index value representing a changing velocity of the concentration of the light-emitting particles using the plurality of the successively measured signal generation time intervals.

11. The non-transitory computer readable storage device of claim 9, in the step of determining the concentration of the light-emitting particle, an index value representing the concentration of the light-emitting particles at an arbitrary time is determined using the plurality of the successively measured signal generation time intervals.

12. The non-transitory computer readable storage device of claim 9, wherein the interval of the generation times of the signals of the light-emitting particles is a time interval in which a predetermined number of the signals of the light-emitting particles have been generated.

* * * * *